(12) United States Patent
Laan et al.

(10) Patent No.: US 8,916,368 B2
(45) Date of Patent: Dec. 23, 2014

(54) LIPASES AND USES THEREOF

(75) Inventors: Jan Metske van der Laan, Breda (NL);
Margot Elisabeth Francoise Schooneveld-Bergmans, Delft (NL)

(73) Assignee: DSM IP Assets B.V., Te Heerlen (NL)

( * ) Notice: Subject to any disclaimer, the term of this patent is extended or adjusted under 35 U.S.C. 154(b) by 1148 days.

(21) Appl. No.: 12/280,353

(22) PCT Filed: Feb. 22, 2007

(86) PCT No.: PCT/EP2007/001693
§ 371 (c)(1),
(2), (4) Date: Sep. 12, 2008

(87) PCT Pub. No.: WO2007/096201
PCT Pub. Date: Aug. 30, 2007

(65) Prior Publication Data
US 2009/0053362 A1    Feb. 26, 2009

(30) Foreign Application Priority Data

Feb. 23, 2006  (EP) .................................. 06110331
Nov. 2, 2006  (EP) .................................. 06123386
Nov. 2, 2006  (EP) .................................. 06123390

(51) Int. Cl.
*C12N 15/81* (2006.01)
*C12P 21/02* (2006.01)
*C12N 9/00* (2006.01)
*C12N 1/19* (2006.01)
*C12N 9/20* (2006.01)

(52) U.S. Cl.
CPC ........................................ *C12N 9/20* (2013.01)
USPC .............. 435/183; 426/23; 426/523; 426/549

(58) Field of Classification Search
None
See application file for complete search history.

(56) References Cited

U.S. PATENT DOCUMENTS

2008/0038404 A1    2/2008  Brunstedt et al.

FOREIGN PATENT DOCUMENTS

| WO | 98/26057 | 6/1998 |
| WO | 2005/087918 | 9/2005 |
| WO | 2006/039541 | 4/2006 |

OTHER PUBLICATIONS

Czymmek et al. "Live-cell imaging of tubulin in the filamentous fungus *Magnaporthe grisea* treated with anti-microtubule and anti-microfilament agents" Protoplasma, vol. 225, pp. 23-32 (Apr. 2005).
Int'l Search Report for PCT/EP2007/001693, mailed Aug. 16, 2007.

*Primary Examiner* — Tekchand Saidha
*Assistant Examiner* — Md. Younus Meah
(74) *Attorney, Agent, or Firm* — Miles & Stockbridge, PC

(57) ABSTRACT

Isolated polypeptide with an amino acid sequence that is at least 95% identical to the amino acid sequence according to SEQ ID NO: 8 or 9.

22 Claims, No Drawings

SEQUENCE LISTING

<160> NUMBER OF SEQ ID NOS: 14

<210> SEQ ID NO 1
<211> LENGTH: 1047
<212> TYPE: DNA
<213> ORGANISM: Magnaporthe grisae

<400> SEQUENCE: 1

| | | |
|---|---|---|
| atgaggttcc ccagcgtgct caccctttg gccacagccc tcacctgctc ggcatcggtt | 60 |
| ctccctgccg gcctgaccta caccaagact gtcgagggcc gcgatgtgac cgtcagcgag | 120 |
| acagacctag acaacttccg tttctatgcg cagtacagcg cggcgaccta ctgcaacgat | 180 |
| gccgccgcct caggggccgc cgtcgcctgc agcaacgacg gatgtcccgc cgtcgtggcc | 240 |
| aacggagcca agatcatccg ttcgctgaac caagacacgt ccaccaacac tgccggctac | 300 |
| cttgcactcg accccaagcg gaagaacatc gtgctcgccc tccgtggctc cacgagcctc | 360 |
| cggaactgga tcaccaacct gactttcctg tggacccgct gcgactttgt ccaggactgc | 420 |
| aagctgcaca cgggctttgc cacagcctgg tcccaggtgc aggccgatgt tctggccgcc | 480 |
| atcgccgacc caaggcccca gaccccgac tacaccgtcg tcgtgacggg ccactccctc | 540 |
| ggcggcgccg tcgccaccgt cgcgggagtc tacctccgcc agctgggcta ccccgtcgag | 600 |
| gtttacacgt acggcagccc gcgcatcggc aatcaggagt tgtgtcagtg ggtttccacg | 660 |
| caggccggca acgtcgagta ccgcgtcacg cacatcgacg accccgtccc ccgcctgccg | 720 |
| cccatcttcc tcggctacag gcacgtcacc cccgagtact ggctcaactc tggcaccctcc | 780 |
| aacacggtca actacaccgt cgccgacatc aaggtctgcg agggcttcgc caacatcaac | 840 |
| tgcaacggcg gcagcctcgg cctcgacaca acgcccacc tctactacct caccgacatg | 900 |
| atcgcctgcg gctccaacaa gttcgtcttc cgccgcgacg acgccaacgc catcagtgac | 960 |
| gccgagctcg agcagaggct gaccatgtac gctcaaatgg atcgcgagtt tgttgctgcg | 1020 |
| cttgaagcca acaagaccgt ggcttaa | 1047 |

<210> SEQ ID NO 2
<211> LENGTH: 1048
<212> TYPE: DNA
<213> ORGANISM: Artificial Sequence
<220> FEATURE:
<223> OTHER INFORMATION: Codon optimised for Aspergillus expression,
      preferably A. niger

<400> SEQUENCE: 2

| | | |
|---|---|---|
| atgcgcttcc cttcggtttt gactctgttg gcgaccgctc tcacctgcag cgcctcggtt | 60 |
| ctgcccgcgg gactcaccta caccaagact gtcgaaggac gcgatgtgac cgtttctgag | 120 |
| actgaccttg acaacttccg tttctacgct cagtactctg ctgcgaccta ctgcaacgat | 180 |
| gccgctgcct ctggtgccgc cgttgcttgc tccaacgacg gctgccccgc ggtcgtggct | 240 |
| aacggcgcca agattatccg ctccctcaac caggatactt ccaccaacac tgctggttac | 300 |
| ctcgccctgg accccaagcg taagaacatt gtccttgctc tgcgtggtag cacctccctc | 360 |
| cgtaactgga tcaccaacct caccttcctc tggacccgtt gcgatttcgt ccaggactgc | 420 |
| aagctgcaca ccggtttcgc caccgcttgg agccaggttc aggccgatgt ccttgcggcc | 480 |
| atcgctgacg ccaaggctca gaaccctgat tacactgtcg tcgtcaccgg ccactccttg | 540 |
| ggcggtgctg tggccaccgt cgccggagtt tacctgcgcc agcttggtta ccctgtggaa | 600 |
| gtctacactt acggctcgcc ccgcatcggc aaccaggagt tcgtccagtg ggtctccact | 660 |

-continued

```
caggccggaa acgtggagta ccgcgtcacc cacatcgacg accccgttcc ccgcttgccc    720
cctatcttcc tcggttaccg tcacgttacc cccgagtact ggctgaacag cggtacttcc    780
aacaccgtca actacaccgt cgccgacatt aaggtctgcg agggtttcgc taacatcaac    840
tgcaacggcg gctctctcgg tctggacacc aacgcccacc tctactacct taccgacatg    900
atcgcctgcg gttccaacaa gttcgtgttc cgccgtgatg acgccaacgc tatctccgat    960
gctgagctcg agcagcgtct gactatgtac gcccagatgg aacgcgactt cgttgccgct   1020
ctcgaggcga acaagaccgt cgcttaaa                                      1048
```

```
<210> SEQ ID NO 3
<211> LENGTH: 1044
<212> TYPE: DNA
<213> ORGANISM: Artificial Sequence
<220> FEATURE:
<223> OTHER INFORMATION: cDNA optimised for A. niger based on sequence
      from M. grisae, having one point mutation

<400> SEQUENCE: 3
atgcgcttcc cctccgtcct gaccctcctt gccactgctc tgacctgctc tgcctccgtc     60
ctccccgctg gtctgaccta caccaagacc gttgagggtc gtgatgtcac cgtctccgag    120
actgacctcg acaacttccg cttctacgct cagtactctg ctgccaccta ctgcaacgat    180
gctgctgcca gcggtgctgc tgttgcttgc tccaacgacg gctgccccgc cgttgttgcc    240
aacggtgcca agatcatccg ctccctcaac caggacacct ccaccaacac tgctggctac    300
ctggctctcg accccaagcg caagaacatt gtccttgctc tccgtggcag cacctcgctg    360
cgcaactgga tcaccaacct ggacttcctc tggactcgct gcgacttcgt ccaggactgc    420
aagctccaca ccggtttcgc cactgcctgg tcccaggtcc aggccgatgt ccttgctgcc    480
attgccgatg ccaaggccca gaaccccgac tacaccgttg ttgtcactgg tcactctctt    540
ggtggtgctg ttgccactgt tgctggtgtc tacctccgcc agctgggcta ccccgttgag    600
gtctacacct acggcagccc tcgtatcggt aaccaggagt tcgtccagtg ggtttctact    660
caggctggca acgtcgagta ccgtgtcacc cacattgatg accccgttcc tcgtcttcct    720
cccatcttcc tgggctaccg ccacgtcacc cccgagtact ggctcaactc cggtacctcc    780
aacaccgtca actacactgt tgccgacatc aaggtctgcg agggtttcgc caacatcaac    840
tgcaacggtg gttccctggg tctcgacacc aacgcccacc tctactacct gaccgacatg    900
attgcctgcg gcagcaacaa gttcgtcttc cgtcgtgatg atgccaacgc catctccgac    960
gccgagctcg agcagcgtct gaccatgtac gctcagatgg accgtgagtt cgtcgctgct   1020
ctcgaggcca acaagaccgt tgcc                                          1044
```

```
<210> SEQ ID NO 4
<211> LENGTH: 1044
<212> TYPE: DNA
<213> ORGANISM: Artificial Sequence
<220> FEATURE:
<223> OTHER INFORMATION: Mutant of sequence obtained from M. grisae

<400> SEQUENCE: 4
atgcgcttcc cctccgtcct gaccctcctt gccactgctc tgacctgctc tgcctccgtc     60
ctccccgctg gtctgaccta caccaagacc gttgagggtc gtgatgtcac cgtctccgag    120
actgacctcg acaacttccg cttctacgct cagtactctg ctgccaccta ctgcaacgat    180
gctgctgcca gcggtgctgc tgttgcttgc tccaacgacg gctgccccgc cgttgttgcc    240
```

```
aacggtgcca agatcatccg ctccctcaac caggacacct ccaccaacac tgctggctac    300
ctggctctcg accccaagcg caagaacatt gtccttgctc tccgtggcag catcaacatc    360
cgcaactggc tgaccaacct ggacttcctc tggactcgct gcgacttcgt ccaggactgc    420
aagctccaca ccggtttcgc cactgcctgg tcccaggtcc aggccgatgt ccttgctgcc    480
attgccgatg ccaaggccca gaaccccgac tacaccgttg ttgtcactgg ccactctctt    540
ggtggtgctg ttgccactgt tgctggtgtc tacctccgcc agcttggata ccccgttgag    600
gtctacacct acggcagccc tcgtatcggt aaccaggagt tcgtccagtg ggtttccacc    660
caggctggca acgtcgagta ccgtgtcacc cacatcgatg accccgttcc tcgtcttcct    720
cctctgatct tcggttaccg tcacgtcacc cccgagtact ggctcaactc cggcacctcc    780
aacaaggtca actacaccgt tgccgacatc aaggtctgcg agggtttcgc caacatcaac    840
tgcaacggtg gctctcttgg tctcgacatt gctgctcacc tgtactacct cactgccatg    900
gatgcctgca cgccggtgg tttcagctgg cgccgtgatg atgccaacgc catctccgac    960
gccgagctcg agcagcgtct gaccatgtac gctcagatgg accgtgagtt cgtcgctgct   1020
ctcgaggcca acaagaccgt tgcc                                          1044
```

<210> SEQ ID NO 5  
<211> LENGTH: 348  
<212> TYPE: PRT  
<213> ORGANISM: Magnaporthe grisae

<400> SEQUENCE: 5

Met Arg Phe Pro Ser Val Leu Thr Leu Leu Ala Thr Ala Leu Thr Cys
1               5                   10                  15

Ser Ala Ser Val Leu Pro Ala Gly Leu Thr Tyr Thr Lys Thr Val Glu
            20                  25                  30

Gly Arg Asp Val Thr Val Ser Glu Thr Asp Leu Asp Asn Phe Arg Phe
        35                  40                  45

Tyr Ala Gln Tyr Ser Ala Ala Thr Tyr Cys Asn Asp Ala Ala Ala Ser
    50                  55                  60

Gly Ala Ala Val Ala Cys Ser Asn Asp Gly Cys Pro Ala Val Val Ala
65                  70                  75                  80

Asn Gly Ala Lys Ile Ile Arg Ser Leu Asn Gln Asp Thr Ser Thr Asn
                85                  90                  95

Thr Ala Gly Tyr Leu Ala Leu Asp Pro Lys Arg Lys Asn Ile Val Leu
            100                 105                 110

Ala Leu Arg Gly Ser Thr Ser Leu Arg Asn Trp Ile Thr Asn Leu Thr
        115                 120                 125

Phe Leu Trp Thr Arg Cys Asp Phe Val Gln Asp Cys Lys Leu His Thr
    130                 135                 140

Gly Phe Ala Thr Ala Trp Ser Gln Val Gln Ala Asp Val Leu Ala Ala
145                 150                 155                 160

Ile Ala Asp Ala Lys Ala Gln Asn Pro Asp Tyr Thr Val Val Thr
                165                 170                 175

Gly His Ser Leu Gly Gly Ala Val Ala Thr Val Ala Gly Val Tyr Leu
            180                 185                 190

Arg Gln Leu Gly Tyr Pro Val Glu Val Tyr Thr Tyr Gly Ser Pro Arg
        195                 200                 205

Ile Gly Asn Gln Glu Phe Val Gln Trp Val Ser Thr Gln Ala Gly Asn
    210                 215                 220

Val Glu Tyr Arg Val Thr His Ile Asp Asp Pro Val Pro Arg Leu Pro

```
            225                 230                 235                 240
    Pro Ile Phe Leu Gly Tyr Arg His Val Thr Pro Glu Tyr Trp Leu Asn
                        245                 250                 255

Ser Gly Thr Ser Asn Thr Val Asn Tyr Thr Val Ala Asp Ile Lys Val
                        260                 265                 270

Cys Glu Gly Phe Ala Asn Ile Asn Cys Asn Gly Gly Ser Leu Gly Leu
                        275                 280                 285

Asp Thr Asn Ala His Leu Tyr Tyr Leu Thr Asp Met Ile Ala Cys Gly
                        290                 295                 300

Ser Asn Lys Phe Val Phe Arg Arg Asp Asp Ala Asn Ala Ile Ser Asp
    305                 310                 315                 320

Ala Glu Leu Glu Gln Arg Leu Thr Met Tyr Ala Gln Met Asp Arg Glu
                        325                 330                 335

Phe Val Ala Ala Leu Glu Ala Asn Lys Thr Val Ala
                        340                 345

<210> SEQ ID NO 6
<211> LENGTH: 314
<212> TYPE: PRT
<213> ORGANISM: Magnaporthe grisae

<400> SEQUENCE: 6

Asp Val Thr Val Ser Glu Thr Asp Leu Asp Asn Phe Arg Phe Tyr Ala
    1               5                   10                  15

Gln Tyr Ser Ala Ala Thr Tyr Cys Asn Asp Ala Ala Ala Ser Gly Ala
                    20                  25                  30

Ala Val Ala Cys Ser Asn Asp Gly Cys Pro Ala Val Val Ala Asn Gly
                35                  40                  45

Ala Lys Ile Ile Arg Ser Leu Asn Gln Asp Thr Ser Thr Asn Thr Ala
            50                  55                  60

Gly Tyr Leu Ala Leu Asp Pro Lys Arg Lys Asn Ile Val Leu Ala Leu
    65                  70                  75                  80

Arg Gly Ser Thr Ser Leu Arg Asn Trp Ile Thr Asn Leu Thr Phe Leu
                    85                  90                  95

Trp Thr Arg Cys Asp Phe Val Gln Asp Cys Lys Leu His Thr Gly Phe
                    100                 105                 110

Ala Thr Ala Trp Ser Gln Val Gln Ala Asp Val Leu Ala Ala Ile Ala
                115                 120                 125

Asp Ala Lys Ala Gln Asn Pro Asp Tyr Thr Val Val Thr Gly His
    130                 135                 140

Ser Leu Gly Gly Ala Val Ala Thr Val Ala Gly Val Tyr Leu Arg Gln
    145                 150                 155                 160

Leu Gly Tyr Pro Val Glu Val Tyr Thr Tyr Gly Ser Pro Arg Ile Gly
                    165                 170                 175

Asn Gln Glu Phe Val Gln Trp Val Ser Thr Gln Ala Gly Asn Val Glu
                    180                 185                 190

Tyr Arg Val Thr His Ile Asp Asp Pro Val Pro Arg Leu Pro Pro Ile
                195                 200                 205

Phe Leu Gly Tyr Arg His Val Thr Pro Glu Tyr Trp Leu Asn Ser Gly
                210                 215                 220

Thr Ser Asn Thr Val Asn Tyr Thr Val Ala Asp Ile Lys Val Cys Glu
    225                 230                 235                 240

Gly Phe Ala Asn Ile Asn Cys Asn Gly Gly Ser Leu Gly Leu Asp Thr
                    245                 250                 255
```

Asn Ala His Leu Tyr Tyr Leu Thr Asp Met Ile Ala Cys Gly Ser Asn
            260                 265                 270

Lys Phe Val Phe Arg Arg Asp Asp Ala Asn Ala Ile Ser Asp Ala Glu
        275                 280                 285

Leu Glu Gln Arg Leu Thr Met Tyr Ala Gln Met Asp Arg Glu Phe Val
290                 295                 300

Ala Ala Leu Glu Ala Asn Lys Thr Val Ala
305                 310

<210> SEQ ID NO 7
<211> LENGTH: 276
<212> TYPE: PRT
<213> ORGANISM: Magnaporthe grisae

<400> SEQUENCE: 7

Asp Val Thr Val Ser Glu Thr Asp Leu Asp Asn Phe Arg Phe Tyr Ala
1               5                   10                  15

Gln Tyr Ser Ala Ala Thr Tyr Cys Asn Asp Ala Ala Ser Gly Ala
            20                  25                  30

Ala Val Ala Cys Ser Asn Asp Gly Cys Pro Ala Val Val Ala Asn Gly
        35                  40                  45

Ala Lys Ile Ile Arg Ser Leu Asn Gln Asp Thr Ser Thr Asn Thr Ala
    50                  55                  60

Gly Tyr Leu Ala Leu Asp Pro Lys Arg Lys Asn Ile Val Leu Ala Leu
65                  70                  75                  80

Arg Gly Ser Thr Ser Leu Arg Asn Trp Ile Thr Asn Leu Thr Phe Leu
                85                  90                  95

Trp Thr Arg Cys Asp Phe Val Gln Asp Cys Lys Leu His Thr Gly Phe
            100                 105                 110

Ala Thr Ala Trp Ser Gln Val Gln Ala Asp Val Leu Ala Ala Ile Ala
        115                 120                 125

Asp Ala Lys Ala Gln Asn Pro Asp Tyr Thr Val Val Thr Gly His
    130                 135                 140

Ser Leu Gly Gly Ala Val Ala Thr Val Ala Gly Val Tyr Leu Arg Gln
145                 150                 155                 160

Leu Gly Tyr Pro Val Glu Val Tyr Thr Tyr Gly Ser Pro Arg Ile Gly
                165                 170                 175

Asn Gln Glu Phe Val Gln Trp Val Ser Thr Gln Ala Gly Asn Val Glu
            180                 185                 190

Tyr Arg Val Thr His Ile Asp Asp Pro Val Pro Arg Leu Pro Pro Ile
        195                 200                 205

Phe Leu Gly Tyr Arg His Val Thr Pro Glu Tyr Trp Leu Asn Ser Gly
    210                 215                 220

Thr Ser Asn Thr Val Asn Tyr Thr Val Ala Asp Ile Lys Val Cys Glu
225                 230                 235                 240

Gly Phe Ala Asn Ile Asn Cys Asn Gly Gly Ser Leu Gly Leu Asp Thr
                245                 250                 255

Asn Ala His Leu Tyr Tyr Leu Thr Asp Met Ile Ala Cys Gly Ser Asn
            260                 265                 270

Lys Phe Val Phe
        275

<210> SEQ ID NO 8
<211> LENGTH: 348
<212> TYPE: PRT
<213> ORGANISM: Artificial Sequence
<220> FEATURE:
<223> OTHER INFORMATION: Point mutation with respect to sequence obtained from M. Grisae

<400> SEQUENCE: 8

```

-continued grisae

<400> SEQUENCE: 9

Asp Val Thr Val Ser Glu Thr Asp Leu Asp Asn Phe Arg Phe Tyr Ala
1               5                   10                  15

Gln Tyr Ser Ala Ala Thr Tyr Cys Asn Asp Ala Ala Ser Gly Ala
            20                  25                  30

Ala Val Ala Cys Ser Asn Asp Gly Cys Pro Ala Val Val Ala Asn Gly
        35                  40                  45

Ala Lys Ile Ile Arg Ser Leu Asn Gln Asp Thr Ser Thr Asn Thr Ala
    50                  55                  60

Gly Tyr Leu Ala Leu Asp Pro Lys Arg Lys Asn Ile Val Leu Ala Leu
65                  70                  75                  80

Arg Gly Ser Thr Ser Leu Arg Asn Trp Ile Thr Asn Leu Asp Phe Leu
                85                  90                  95

Trp Thr Arg Cys Asp Phe Val Gln Asp Cys Lys Leu His Thr Gly Phe
            100                 105                 110

Ala Thr Ala Trp Ser Gln Val Gln Ala Asp Val Leu Ala Ala Ile Ala
        115                 120                 125

Asp Ala Lys Ala Gln Asn Pro Asp Tyr Thr Val Val Thr Gly His
    130                 135                 140

Ser Leu Gly Gly Ala Val Ala Thr Val Ala Gly Val Tyr Leu Arg Gln
145                 150                 155                 160

Leu Gly Tyr Pro Val Glu Val Tyr Thr Tyr Gly Ser Pro Arg Ile Gly
                165                 170                 175

Asn Gln Glu Phe Val Gln Trp Val Ser Thr Gln Ala Gly Asn Val Glu
            180                 185                 190

Tyr Arg Val Thr His Ile Asp Asp Pro Val Pro Arg Leu Pro Pro Ile
        195                 200                 205

Phe Leu Gly Tyr Arg His Val Thr Pro Glu Tyr Trp Leu Asn Ser Gly
    210                 215                 220

Thr Ser Asn Thr Val Asn Tyr Thr Val Ala Asp Ile Lys Val Cys Glu
225                 230                 235                 240

Gly Phe Ala Asn Ile Asn Cys Asn Gly Gly Ser Leu Gly Leu Asp Thr
                245                 250                 255

Asn Ala His Leu Tyr Tyr Leu Thr Asp Met Ile Ala Cys Gly Ser Asn
            260                 265                 270

Lys Phe Val Phe
        275

<210> SEQ ID NO 10
<211> LENGTH: 348
<212> TYPE: PRT
<213> ORGANISM: Artificial Sequence
<220> FEATURE:
<223> OTHER INFORMATION: Mutant of sequence obtained from M. grisae

<400> SEQUENCE: 10

Met Arg Phe Pro Ser Val Leu Thr Leu Leu Ala Thr Ala Leu Thr Cys
1 5 10 15

Ser Ala Ser Val Leu Pro Ala Gly Leu Thr Tyr Thr Lys Thr Val Glu
20 25 30

Gly Arg Asp Val Thr Val Ser Glu Thr Asp Leu Asp Asn Phe Arg Phe
35 40 45

Tyr Ala Gln Tyr Ser Ala Ala Thr Tyr Cys Asn Asp Ala Ala Ala Ser
50 55 60

```
Gly Ala Ala Val Ala Cys Ser Asn Asp Gly Cys Pro Ala Val Val Ala
 65                  70                  75                  80

Asn Gly Ala Lys Ile Ile Arg Ser Leu Asn Gln Asp Thr Ser Thr Asn
                 85                  90                  95

Thr Ala Gly Tyr Leu Ala Leu Asp Pro Lys Arg Lys Asn Ile Val Leu
            100                 105                 110

Ala Leu Arg Gly Ser Ile Asn Ile Arg Asn Trp Leu Thr Asn Leu Asp
        115                 120                 125

Phe Leu Trp Thr Arg Cys Asp Phe Val Gln Asp Cys Lys Leu His Thr
130                 135                 140

Gly Phe Ala Thr Ala Trp Ser Gln Val Gln Ala Asp Val Leu Ala Ala
145                 150                 155                 160

Ile Ala Asp Ala Lys Ala Gln Asn Pro Asp Tyr Thr Val Val Val Thr
                165                 170                 175

Gly His Ser Leu Gly Gly Ala Val Ala Thr Val Ala Gly Val Tyr Leu
            180                 185                 190

Arg Gln Leu Gly Tyr Pro Val Glu Val Tyr Thr Tyr Gly Ser Pro Arg
        195                 200                 205

Ile Gly Asn Gln Glu Phe Val Gln Trp Val Ser Thr Gln Ala Gly Asn
210                 215                 220

Val Glu Tyr Arg Val Thr His Ile Asp Asp Pro Val Pro Arg Leu Pro
225                 230                 235                 240

Pro Leu Ile Phe Gly Tyr Arg His Val Thr Pro Glu Tyr Trp Leu Asn
                245                 250                 255

Ser Gly Thr Ser Asn Lys Val Asn Tyr Thr Val Ala Asp Ile Lys Val
            260                 265                 270

Cys Glu Gly Phe Ala Asn Ile Asn Cys Asn Gly Gly Ser Leu Gly Leu
        275                 280                 285

Asp Ile Ala Ala His Leu Tyr Tyr Leu Thr Ala Met Asp Ala Cys Asn
290                 295                 300

Ala Gly Gly Phe Ser Trp Arg Arg Asp Asp Ala Asn Ala Ile Ser Asp
305                 310                 315                 320

Ala Glu Leu Glu Gln Arg Leu Thr Met Tyr Ala Gln Met Asp Arg Glu
                325                 330                 335

Phe Val Ala Ala Leu Glu Ala Asn Lys Thr Val Ala
            340                 345

<210> SEQ ID NO 11
<211> LENGTH: 276
<212> TYPE: PRT
<213> ORGANISM: Artificial Sequence
<220> FEATURE:
<223> OTHER INFORMATION: Mutant of sequence obtained from M. grisae

<400> SEQUENCE: 11

Asp Val Thr Val Ser Glu Thr Asp Leu Asp Asn Phe Arg Phe Tyr Ala
  1               5                  10                  15

Gln Tyr Ser Ala Ala Thr Tyr Cys Asn Asp Ala Ala Ser Gly Ala
             20                  25                  30

Ala Val Ala Cys Ser As

```
Arg Gly Ser Ile Asn Ile Arg Asn Trp Leu Thr Asn Leu Asp Phe Leu
            85                  90                  95

Trp Thr Arg Cys Asp Phe Val Gln Asp Cys Lys Leu His Thr Gly Phe
            100                 105                 110

Ala Thr Ala Trp Ser Gln Val Gln Ala Asp Val Leu Ala Ala Ile Ala
            115                 120                 125

Asp Ala Lys Ala Gln Asn Pro Asp Tyr Thr Val Val Thr Gly His
    130                 135                 140

Ser Leu Gly Gly Ala Val Ala Thr Val Ala Gly Val Tyr Leu Arg Gln
145                 150                 155                 160

Leu Gly Tyr Pro Val Glu Val Tyr Thr Tyr Gly Ser Pro Arg Ile Gly
                165                 170                 175

Asn Gln Glu Phe Val Gln Trp Val Ser Thr Gln Ala Gly Asn Val Glu
            180                 185                 190

Tyr Arg Val Thr His Ile Asp Asp Pro Val Pro Arg Leu Pro Pro Leu
            195                 200                 205

Ile Phe Gly Tyr Arg His Val Thr Pro Glu Tyr Trp Leu Asn Ser Gly
    210                 215                 220

Thr Ser Asn Lys Val Asn Tyr Thr Val Ala Asp Ile Lys Val Cys Glu
225                 230                 235                 240

Gly Phe Ala Asn Ile Asn Cys Asn Gly Gly Ser Leu Gly Leu Asp Ile
                245                 250                 255

Ala Ala His Leu Tyr Tyr Leu Thr Ala Met Asp Ala Cys Asn Ala Gly
                260                 265                 270

Gly Phe Ser Trp
        275

<210> SEQ ID NO 12
<211> LENGTH: 275
<212> TYPE: PRT
<213> ORGANISM: Artificial Sequence
<220> FEATURE:
<223> OTHER INFORMATION: Mutant of sequence obtained from M. grisae

<400> SEQUENCE: 12

Asp Val Thr Val Ser Glu Thr Asp Leu Asp Asn Phe Arg Phe Tyr Ala
1               5                   10                  15

Gln Tyr Ser Ala Ala Thr Tyr Cys Asn Asp Ala Ala Ser Gly Ala

```
Leu Gly Tyr Pro Val Glu Val Tyr Thr Tyr Gly Ser Pro Arg Ile Gly
            165                 170                 175

Asn Gln Glu Phe Val Gln Trp Val Ser Thr Gln Ala Gly Asn Val Glu
        180                 185                 190

Tyr Arg Val Thr His Ile Asp Asp Pro Val Pro Arg Leu Pro Pro Leu
    195                 200                 205

Ile Phe Gly Tyr Arg His Val Thr Pro Glu Tyr Trp Leu Asn Ser Gly
210                 215                 220

Thr Ser Asn Lys Val Asn Tyr Thr Val Ala Asp Ile Lys Val Cys Glu
225                 230                 235                 240

Gly Phe Ala Asn Ile Asn Cys Asn Gly Gly Ser Leu Gly Leu Asp Ile
            245                 250                 255

Ala Ala His Leu Tyr Tyr Leu Thr Ala Met Asp Ala Cys Asn Ala Gly
        260                 265                 270

Gly Phe Ser
        275

<210> SEQ ID NO 13
<211> LENGTH: 274
<212> TYPE: PRT
<213> ORGANISM: Artificial Sequence
<220> FEATURE:
<223> OTHER INFORMATION: Mutant of sequence obtained from M. grisae

<400> SEQUENCE:

```
Gly Phe Ala Asn Ile Asn Cys Asn Gly Gly Ser Leu Gly Leu Asp Ile
            245                 250                 255

Ala Ala His Leu Tyr Tyr Leu Thr Ala Met Asp Ala Cys Asn Ala Gly
            260                 265                 270

Gly Phe

<210> SEQ ID NO 14
<211> LENGTH: 314
<212> TYPE: PRT
<213> ORGANISM: Artificial Sequence
<220> FEATURE:
<223> OTHER INFORMATION: Mutant of sequence obtained from M. grisae

<400> SEQUENCE: 14

Asp Val Thr Val Ser Glu Thr Asp Leu Asp Asn Phe Arg Phe Tyr Ala
1               5                   10                  15

Gln Tyr Ser Ala Ala Thr Tyr Cys Asn Asp Ala Ala Ser Gly Ala
            20                  25                  30

Ala Val Ala Cys Ser Asn Asp Gly Cys Pro Ala Val Val Ala Asn Gly
            35                  40                  45

Ala Lys Ile Ile Arg Ser Leu Asn Gln Asp Thr Ser Thr Asn Thr Ala
    50                  55                  60

Gly Tyr Leu Ala Leu Asp Pro Lys Arg Lys Asn Ile Val Leu Ala Leu
65                  70                  75                  80

Arg Gly Ser Ile Asn Ile Arg Asn Trp Leu Thr Asn Leu Asp Phe Leu
                85                  90                  95

Trp Thr Arg Cys Asp Phe Val Gln Asp Cys Lys Leu His Thr Gly Phe
            100                 105                 110

Ala Thr Ala Trp Ser Gln Val Gln Ala Asp Val Leu Ala Ala Ile Ala
        115                 120                 125

Asp Ala Lys Ala Gln Asn Pro Asp Tyr Thr Val Val Val Thr Gly His
    130                 135                 140

Ser Leu Gly Gly Ala Val Ala Thr Val Ala Gly Val Tyr Leu Arg Gln
145                 150                 155                 160

Leu Gly Tyr Pro Val Glu Val Tyr Thr Tyr Gly Ser Pro Arg Ile Gly
                165                 170                 175

Asn Gln Glu Phe Val Gln Trp Val Ser Thr Gln Ala Gly Asn Val Glu
            180                 185                 190

Tyr Arg Val Thr His Ile Asp Asp Pro Val Pro Arg Leu Pro Pro Leu
        195                 200                 205

Ile Phe Gly Tyr Arg His Val Thr Pro Glu Tyr Trp Leu Asn Ser Gly
    210                 215                 220

Thr Ser Asn Lys Val Asn Tyr Thr Val Ala Asp Ile Lys Val Cys Glu
225                 230                 235                 240

Gly Phe Ala Asn Ile Asn Cys Asn Gly Gly Ser Leu Gly Leu Asp Ile
                245                 250                 255

Ala Ala His Leu Tyr Tyr Leu Thr Ala Met Asp Ala Cys Asn Ala Gly
            260                 265                 270

Gly Phe Ser Trp Arg Arg Asp Asp Ala Asn Ala Ile Ser Asp Ala Glu
        275                 280                 285

Leu Glu Gln Arg Leu Thr Met Tyr Ala Gln Met Asp Arg Glu Phe Val
    290                 295                 300

Ala Ala Leu Glu Ala Asn Lys Thr Val Ala
305                 310
```

LIPASES AND USES THEREOF

This application is the U.S. national phase of International Application No. PCT/EP2007/001693, filed 22 Feb. 2007, which designated the U.S. and claims priority to European Application Nos. 06110331.3, filed 23 Feb. 2006; 06123386.2, filed 2 Nov. 2006; and 06123390.4, filed 2 Nov. 2006; the entire contents of each of which are hereby incorporated by reference.

FIELD OF THE INVENTION

The invention relates to newly identified polynucleotide sequences comprising genes that encode a novel lipolytic enzyme. The enzymes may be isolated from *Magnaporthe grisae*. The invention features the full length coding sequence of the novel gene as well as the amino acid sequence of the full-length functional protein and functional equivalents of the gene or the amino acid sequence. The invention also relates to methods of using these proteins in industrial processes, for example in baking industry. Also included in the invention are cells transformed with a polynucleotide according to the invention suitable for producing these proteins and cells wherein a protein according to the invention is genetically modified to enhance or reduce its activity and/or level of expression.

BACKGROUND OF THE INVENTION

In order to improve the handling properties of the dough and/or the final properties of the baked products there is a continuous effort to develop processing aids with improving properties. Processing aids are defined herein as compounds that improve the handling properties of the dough and/or the final properties of the baked products. Dough properties that may be improved comprise stability, machineability, gas retaining capability, reduced blistering, reduced stickiness, elasticity, extensibility, moldability etcetera. Properties of the baked products that may be improved comprise loaf volume, crust crispiness, crumb texture, crumb structure, crumb softness, flavour relative staleness and shelf life. These dough and/or baked product improving processing aids can be divided into two groups: chemical additives and enzymes (also referred to as baking enzymes).

Chemical additives with improving properties comprise oxidising agents such as ascorbic acid, bromate and azodicarbonate, reducing agents such as L-cysteine and glutathione, emulsifiers acting as dough conditioners such as diacetyl tartaric acid esters of mono/diglycerides (DATEM), sodium stearoyl lactylate (SSL) or calcium stearoyl lactylate (CSL), or acting as crumb softeners such as glycerol monostearate (GMS) etceteras, fatty materials such as triglycerides (fat) or lecithin and others.

As a result of a consumer-driven need to replace the chemical additives by more natural products, several baking enzymes have been developed with dough and/or baked product improving properties and which are used in all possible combinations depending on the specific baking application conditions.

Emulsifiers, applied in baking industry can be roughly divided in crumb softening or dough strengthening agents. Distilled monoglycerides are used mainly for crumb softening. Complexing of the monoglycerides with starch prevents complete recrystallisation of starch, which results in initial crumb softness and/or reduction of crumb firming rate during shelf life of the baked product. For dough strengthening, a few different synthetic analogues of polar lipids are applied, such as DATEM, CSL and SSL. Their effect in breadmaking is to improve dough stability, increase loaf volume and induce a fine and uniform crumb structure. With regard to this latter aspect it should be noted that crumb softening is also included when these emulsifiers are applied. Also reduced stickiness of the dough, improved machinability of the dough, increased loaf volume of the baked product, improved crumb structure, improved crumb softness, improved crispyness of the crust can be reached.

The emulsifiers, due to their polar and apolar moieties, can concentrate at oil-water and gas-water interfaces. In breadmaking the gas cells are initially enclosed in a gluten-starch matrix, but during fermentation gas cells increase in volume and interfaces between gas cells comprise only a liquid film of surface-active material. The endogenous polar lipids of wheat flour are present in these liquid films, as well as the added emulsifiers. It is known that polar diacylglycerols, such as lecithins or DATEM produced from diacylglycerols, have only limited effect in breadmaking, when compared to their monoacylglycerol counterparts.

It is known in the art that certain lipolytic enzymes can be used as DATEM replacers such as for example is disclosed by L. Chirstiansen et al in Proceedings of the Third Symposium on Enzymes in Grain Processing, 25-27 Sep. 2002, p 269-274.

Lipolytic enzymes are enzymes that catalyse the hydrolysis of ester bonds in lipid substrates. Lipolytic enzymes can act upon several types of lipids, ranging from glycerides (e.g. triglycerides), phospholipids, sphingoplipids or glycolipids, such as galactolipids.

Glycerides are esters of glycerol and fatty acids. Triglycerides (also known as triacylglycerol or triacylglycerides) are mostly present in vegetable oils and animal fat. Lipases (EC 3.1.1.3) are defined herein as enzymes that hydrolyse one or more of the fatty acids from lipids, more specifically they hydrolyse the ester bond between fatty acid and hydroxyl groups of the glycerol.

Galactolipids consist of a glycerol backbone with two esterified fatty acids in an outer (sn-1) and middle (sn-2) position, while the third hydroxyl group is bound to sugar residues such as a galactose, for example monogalacosyldiglyceride or digalactosyldiglyceride. Galactolipase (EC 3.1.1.26) catalyses the hydrolysis of one or both fatty acyl group(s) in the sn-1 and sn-2 positions respectively from a galactosyldiglyceride.

Phospholipids consist of a glycerol backbone with two esterified fatty acids in an outer (sn-1) and the middle (sn-2) position, while the third hydroxyl group of the glycerol is esterified with phosphoric acid. The phosphoric acid may, in turn, be esterified to for example an amino alcohol like ethanolamine (phosphatidylethanolamine), choline (phosphatidylcholine). Phospholipases are defined herein as enzymes that participate in the hydrolysis of one or more bonds in the phospholipids.

Lipolytic enzymes comprise for example lipases, galactolipases and phospholipases, such as for example phospholipase A1, A2 and lysophospholipase, depending on the substrate they act upon.

There is a continuing need for improved lipolytic enzymes that can be used as replacers of chemical emulsifiers, such as DATEM, CSL and SSL, in the production of bread.

OBJECT OF THE INVENTION

It is the object of the present invention to provide a novel lipolytic enzyme which is suitable to be used as an enzymatic substitute for chemical emulsifiers. Furthermore, it is an object of the invention to provide novel polynucleotides encoding the novel lipolytic enzyme. A further object is to provide naturally and recombinantly produced lipolytic enzyme as well as recombinant strains producing these. Also fusion polypeptides are part of the invention as well as methods of making and using the polynucleotides and polypeptides according to the invention.

SUMMARY OF THE INVENTION

The present invention provides a novel lipolytic enzyme which is suitable to be used as an enzymatic substitute for chemical emulsifiers. Surprisingly, the novel lipolytic enzyme is extremely suitable for use as substitute for chemical emulsifiers, since the enzyme has at least one of the following properties in situ when used in dough:
  a relatively low activity towards apolar lipids
  a relatively high activity towards polar diacyl-lipids, at least towards diacyl galactolipids
  a relatively low activity towards polar monoacyl compounds.
For example, the enzyme according to the invention can show in situ a relatively low lysophospholipase activity and a relatively low lipase activity. These unexpected properties are all found to be advantageous when used as a replacer of chemical emulsifiers in dough.

The novel lipolytic enzyme yields one or more improved dough and/or baked product properties if used herein, selected from the group of increased strength of the dough, increased elasticity of the dough, increased stability of the dough, reduced stickiness of the dough, improved extensibility of the dough, improved machineability of the dough, increased volume of the baked product, improved crumb structure of the baked product, reduced blistering of the baked product, improved softness of the baked product, improved anti-staling of the baked product, improved crust of the baked product or which have a broad substrate specificity.

The invention furthermore provides for novel polynucleotides encoding novel lipolytic enzyme.

In particular, the invention provides for polynucleotides having a nucleotide sequence that hybridizes preferably under high stringent conditions to a sequence according to any one of SEQ ID NO: 2, SEQ ID NO: 3 or SEQ ID NO: 4 (herein after referred to as "SEQ ID NO: 2-4"). Consequently, the invention provides nucleic acids that are at least 85%, preferably at least 88%, more preferably at least 90%, even more preferably at least 95%, 96%, 97%, 98% or 99% homologous to the sequence according to SEQ ID NO: 2, SEQ ID NO: 3 or SEQ ID NO: 4.

In one embodiment the invention provides for such an isolated polynucleotide obtainable from a filamentous fungus, in particular *Magnaporthe* is preferred and even more preferred *Magnaporthe grisae*.

In a further embodiment such isolated polynucleotide can be obtained synthetically by the methods known to the person skilled in the art.

In yet another embodiment, the invention provides for an isolated polynucleotide comprising a nucleic acid sequence encoding a polypeptide with an amino acid sequence as shown in SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 (herein after referred to as "SEQ ID NO: 5-14") or functional equivalents of any of them.

In a further embodiment, the invention provides an isolated polynucleotide encoding at least one functional domain of a polypeptide according to any one of SEQ ID NO: 5-14 or functional equivalents thereof.

In another embodiment the invention provides a lipolytic enzyme gene according to any one of SEQ ID NO: 2-4 or variants or fragments thereof that are still coding for active enzyme.

The invention also relates to vectors comprising a polynucleotide sequence according to the invention and primers, probes and fragments that may be used to amplify or detect the DNA according to the invention.

In a further preferred embodiment, a vector is provided wherein the polynucleotide sequence according to the invention is functionally linked with at least one regulatory sequence suitable for expression of the encoded amino acid sequence in a suitable host cell, such as *Aspergillus*, more specifically *Aspergillus niger, oryzae* or *nidulans*. Preferably the host cell is *Aspergillus niger*. The invention also provides methods for preparing polynucleotides and vectors according to the invention.

The invention also relates to recombinantly produced host cells that contain heterologous or homologous polynucleotides according to the invention.

In another embodiment, the invention provides recombinant host cells wherein the expression of a lipolytic enzyme according to the invention is significantly increased or wherein the activity of the lipolytic enzyme is increased.

In another embodiment the invention provides for a recombinantly produced host cell that contains heterologous or homologous DNA according to the invention and wherein the cell is capable of producing a functional lipolytic enzyme according to the invention, preferably a cell capable of overexpressing the lipolytic enzyme according to the invention, for example an *Aspergillus* strain comprising an increased copy number of a gene according to the invention.

In yet another aspect of the invention, a purified polypeptide is provided. The polypeptides according to the invention include the polypeptides encoded by the polynucleotides according to the invention. Especially preferred is a polypeptide according to any one of SEQ ID NO: 5-14 or functional equivalents of any of them.

Fusion proteins comprising a polypeptide according to the invention are also within the scope of the invention. The invention also provides methods of making the polypeptides according to the invention.

The invention also relates to the use of the lipolytic enzyme according to the invention in any industrial process as described herein.

DETAILED DESCRIPTION OF THE INVENTION

Polynucleotides

In one embodiment, the present invention provides polynucleotides encoding lipolytic enzymes, tentatively called LIP01, having an amino acid sequence according to any one of SEQ ID NO: 5, SEQ ID NO: 6, SEQ ID NO: 7 (herein after referred to as "SEQ ID NO: 5-7") or functional equivalents of any of them. In another embodiment, the invention provides polynucleotides encoding lipolytic enzymes, tentatively called LIP02, having an amino acid sequence according to any one of SEQ ID NO: 8, SEQ ID NO: 9 (herein after referred to as "SEQ ID NO: 8-9") or functional equivalents of any of them. In a further embodiment, the invention provides polynucleotides encoding lipolytic enzymes, tentatively called LIP03, having an amino acid sequence according to any one of SEQ ID NO: 10, SEQ ID NO: 11, SEQ ID NO: 12;

SEQ ID NO: 13; SEQ ID NO: 14 (herein after referred to as "SEQ ID NO: 10-14") or functional equivalents of any of them.

The sequence of the gene encoding LIP01 was determined by sequencing a genomic clone obtained from *Magnaporthe grisae* according to SEQ ID NO: 1. The sequence of the genes encoding LIP02 and LIP03 were obtained by mutating a genomic clone obtained from *Magnaporthe grisae* according to SEQ ID NO: 1. The LIP02 constitutes of a point mutation with respect to LIP01. The invention provides polynucleotide sequences comprising the gene encoding the LIP01-LIP03 lipolytic enzyme as well as its coding sequence. Accordingly, the invention relates to an isolated polynucleotide comprising the nucleotide sequence according to any one of SEQ ID NO: 2-4 or functional equivalents thereof.

In particular, the invention relates to an isolated polynucleotide hybridisable under stringent conditions, preferably under high stringent conditions, to a polynucleotide according to SEQ ID NO: 2-4.

Advantageously, such isolated polynucleotide may be obtained from filamentous fungi, in particular from Magnaporthaceae, such as *Magnaporthe*, for example *grisae, oryzae, poae, rhizophila, salvinii*, preferably from *Magnaporthe grisae*. More specifically, the invention relates to an isolated polynucleotide having a nucleotide sequence according to SEQ ID NO: 2.

In another embodiment according to the invention, the invention relates to an isolated polynucleotide hybridisable under stringent conditions, preferably under high stringent conditions, to a polynucleotide according to SEQ ID NO: 3 or SEQ ID NO: 4. Such isolated polynucleotide may be obtained by synthesis with methods known to the person skilled in the art. Even more advantageously, such isolated polynucleotide may be obtained by mutating a polynucleotide obtained from filamentous fungi, in particular from Magnaporthaceae, such as *Magnaporthe*, for example *grisae, oryzae, poae, rhizophila, salvinii*, preferably from *Magnaporthe grisae*, and most preferably a polynucleotide comprising a nucleotide sequence according to SEQ ID NO: 1 or SEQ ID NO: 2.

The invention also relates to an isolated polynucleotide encoding at least one functional domain of a polypeptide according to any one of SEQ ID NO: 5-14 or functional equivalents of any of them.

As used herein, the terms "gene" and "recombinant gene" refer to nucleic acid molecules which may be isolated from chromosomal DNA, which include an open reading frame encoding a protein, e.g. a *Magnaporthe grisae* lipolytic enzyme. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence of any one of SEQ ID NO: 2-4 or a functional equivalent thereof, can be isolated using standard molecular biology techniques and the sequence information provided herein. For example, using all or portion of the nucleic acid sequence of any one of SEQ ID NO: 2-4 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of any one of SEQ ID NO: 2-4 can be isolated by the polymerase chain reaction (PCR) using synthetic oligonucleotide primers designed based upon the sequence information contained in any one of SEQ ID NO: 2-4.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

In a preferred embodiment, an isolated nucleic acid molecule of the invention comprises the nucleotide sequence shown in any one of SEQ ID NO: 2-4. The sequence of SEQ ID NO: 2 corresponds to the a coding region of the lipolytic enzyme cDNA based on the genomic DNA according to SEQ ID NO: 1. This cDNA comprises sequences encoding the *Magnaporthe grisae* LIP01 according to any one of SEQ ID NO: 5-7.

In another preferred embodiment, an isolated nucleic acid molecule of the invention comprises a nucleic acid molecule which is a complement of the nucleotide sequence shown in SEQ ID NO: 2-4 or a functional equivalent of these nucleotide sequences.

A nucleic acid molecule which is complementary to another nucleotide sequence is one which is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promoter) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule which is antisense to a LIP01-LIP03 nucleic acid molecule, e.g., the coding strand of a LIP01-LIP03 nucleic acid molecule. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from filamentous fungi, in particular *Magnaporthe grisae* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence according to any one of SEQ ID NO: 2-4, for example a fragment which can be used as a probe or primer or a fragment encoding a portion of a LIP01-LIP03 protein. The nucleotide sequence determined from the cloning of the LIP01-LIP03 gene and cDNA allows for the generation of probes and primers designed for use in identifying and/or cloning other LIP01-LIP03 family members, as well as LIP01-LIP03 homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence according to any one of SEQ ID NO: 2-4 or of a functional equivalent thereof.

Probes based on the LIP01-LIP03 nucleotide sequences can be used to detect transcripts or genomic LIP01-LIP03 sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells which express a LIP01-LIP03 protein.

Identity & Homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

The skilled person will be aware of the fact that several different computer programs are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wusch (J. Mol. Biol. (48): 444-453 (1970)) algorithm which has been incorporated into the GAP program in the Accelrys GCG software package (available at http colon forward slash forward slash www dot accelrys dot com forward slash products forward slash gcg forward slash), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the Accelrys GCG software package (available at http colon forward slash forward slash www dot accelrys dot corn forward slash products forward slash gcg forward slash), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at the ALIGN Query using sequence data of the Genestream server IGH Montpellier France http://vega.igh.cnrs.fr/bin/align-guess.cgi) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to LIP01-LIP03 nucleic acid molecules of the invention. BLAST protein searches can be performed with the XBLAST program, score=50, wordlength=3 to obtain amino acid sequences homologous to LIP01-LIP03 protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at http colon forward slash forward slash www dot ncbi dot nlm dot nih dot gov forward slash.

Hybridisation

As used herein, the term "hybridizing" is intended to describe conditions for hybridization and washing under which nucleotide sequences at least about 60%, at least about 70%, at least about 80%, more preferably at least about 85%, even more preferably at least about 90%, most preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

Obtaining Full Length DNA from Other Organisms

In a typical approach, cDNA libraries constructed from other organisms, e.g. filamentous fungi, in particular from the species *Magnaporthe* can be screened.

For example, *Magnaporthe* strains can be screened for homologous LIP01-LIP03 polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a LIP01-LIP03 polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new LIP01-LIP03 nucleic acid sequence, or a functional equivalent thereof.

The PCR fragment can then be used to isolate a full-length cDNA clone by a variety of known methods. For example, the amplified fragment can be labeled and used to screen a bacteriophage or cosmid cDNA library. Alternatively, the labeled fragment can be used to screen a genomic library.

PCR technology also can be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, preferably expression vectors, containing a nucleic acid encoding a LIP01-LIP03 protein or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. LIP01-LIP03 proteins, mutant forms of LIP01-LIP03 proteins, fragments, variants or functional equivalents thereof, fusion proteins, etc.).

The recombinant expression vectors of the invention can be designed for expression of LIP01-LIP03 proteins in prokaryotic or eukaryotic cells. For example, LIP01-LIP03 proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled person. In a specific embodiment, promoters are preferred that are capable of directing a high expression level of lipolytic enzyme in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2$^{nd}$, ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methatrexate. Nucleic acid encoding a selectable marker can be introduced into a host cell on the same vector as that encoding a LIP01-LIP03 protein or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

As indicated, the expression vectors will preferably contain selectable markers. Such markers include dihydrofolate reductase or neomycin resistance for eukarotic cell culture and tetracyline or ampicilling resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture mediums and conditions for the above-described host cells are known in the art.

Vectors preferred for use in bacteria are for example disclosed in WO-A1-2004/074468, which are hereby enclosed by reference. Other suitable vectors will be readily apparent to the skilled artisan.

Known bacterial promoters suitable for use in the present invention include the promoters disclosed in WO-A1-2004/074468, which are hereby enclosed by reference.

Transcription of the DNA encoding the polypeptides of the present invention by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

The LIP01-LIP03 polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having the amino acid sequence according to any one of SEQ ID NO: 5-14, and an amino acid sequence obtainable by expressing the polynucleotide of any one of SEQ ID NO: 2-4 in an appropriate host. Also, a peptide or polypeptide comprising a functional equivalent of the above polypeptides is comprised within the present invention.

As is known to the person skilled in the art it is possible that the N-termini of SEQ ID NO: 5-14 might be heterologous as well as the C-terminus of SEQ ID NO: 5-14, due to processing errors during maturation. In particular such processing errors might occur upon overexpression of the polypeptide. In addition, exo-protease activity might give rise to heterogeneity. The extent to which heterogeneity occurs depends also on the host and fermentation protocols that are used. Such C-terminal processing artefacts might lead to shorter polypeptides or longer polypeptides as indicated with SEQ ID NO: 5-14. As a result of such errors the N-terminus might also be heterologous.

In a further embodiment, the invention provides an isolated polynucleotide encoding at least one functional domain of a polypeptide according to any one of SEQ ID NO: 5-14 contain additional residues and start at position −1, or −2, or −3 etc. Alternatively, it might lack certain residues and as a consequence start at position 2, or 3, or 4 etc.

More specifically for LIP01, in one embodiment of the invention SEQ ID NO: 5 discloses the protein as directly translated from the cDNA as given in SEQ ID NO: 2. Usually such protein will be processed before yielding a mature protein and will for example loose a signal sequence, preferably thereby yielding SEQ ID NO: 6 or 7. For the amino acid sequence as shown in SEQ ID NO: 6 and SEQ ID NO: 7, the N-terminus in case it contains additional residues might contain the following additional amino acid sequences R, GR or EGR, corresponding to a start of the N-terminus on positions −1, −2 or −3 respectively. Analogous the C-terminal processing artefacts might lead to shorter polypeptides or longer polypeptides. In the specific case of SEQ ID NO: 7, the C-terminus in case it contains additional residues preferably contains the following additional amino acid sequences R, RR or RRD, corresponding to a prolonged C-terminus on positions 310+1, +2 or +3 respectively.

More specifically for LIP02, in yet another embodiment, the invention provides for an isolated polynucleotide comprising a nucleic acid sequence encoding a polypeptide with an amino acid sequence as shown in SEQ ID NO: 9 or functional equivalents of any of them. SEQ ID NO: 8 discloses the protein as directly translated from the cDNA as given in SEQ ID NO: 3. Usually such protein will be processed before yielding a mature protein and will for example loose a signal sequence, preferably thereby yielding SEQ ID NO: 9. It might be that the C- and N-termini of the resulting protein are heterologous, for example due to processing artefacts.

More specifically for LIP03, in yet another embodiment, SEQ ID NO: 10 discloses the protein as directly translated from the cDNA as given in SEQ ID NO: 4. Usually such protein will be processed before yielding a mature protein and will for example loose a signal sequence, preferably thereby yielding SEQ ID NO: 11, 12, 13 or 14.

The above polypeptides are collectively comprised in the term "polypeptides according to the invention".

The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The LIP01-LIP03 lipolytic enzyme according to the invention can be recovered and purified from recombinant cell cultures by methods known in the art (Protein Purification Protocols, Methods in Molecular Biology series by Paul Cutler, Humana Press, 2004).

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Protein Fragments

The invention also features biologically active fragments of the polypeptides according to the invention.

Biologically active fragments of a polypeptide of the invention include polypeptides comprising amino acid sequences sufficiently identical to or derived from the amino acid sequence of the LIP01-LIP03 protein (e.g., the amino acid sequence of SEQ ID NO: 5-14, which include fewer amino acids than the full length protein but which exhibit at least one biological activity of the corresponding full-length protein. Typically, biologically active fragments comprise a domain or motif with at least one activity of the LIP01-LIP03 protein. A biologically active fragment of a protein of the invention can be a polypeptide which is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments which encode the above biologically active fragments of the LIP01-LIP03 protein.

Fusion Proteins

The proteins of the present invention or functional equivalents thereof, e.g., biologically active portions thereof, can be operatively linked to a non-LIP01-LIP03 polypeptide (e.g., heterologous amino acid sequences) to form fusion proteins. A "non-LIP01-LIP03 polypeptide" refers to a polypeptide having an amino acid sequence corresponding to a protein which is not substantially homologous to the LIP01-LIP03 protein. Such "non-LIP01-LIP03 polypeptide" can be derived from the same or a different organism. Within a LIP01-LIP03 fusion protein the LIP01-LIP03 polypeptide can correspond to all or a biologically active fragment of a LIP01-LIP03 protein. In a preferred embodiment, a LIP01-LIP03 fusion protein comprises at least two biologically active portions of a LIP01-LIP03 protein. Within the fusion protein, the term "operatively linked" is intended to indicate that the LIP01-LIP03 polypeptide and the non-LIP01-LIP03 polypeptide are fused in-frame to each other. The non-LIP01-LIP03 polypeptide can be fused to the N-terminus or C-terminus of the LIP01-LIP03 polypeptide.

For example, in one embodiment, the fusion protein is a GST-LIP01-LIP03 fusion protein in which the LIP01-LIP03 sequences are fused to the C-terminus of the GST sequences. Such fusion proteins can facilitate the purification of recombinant LIP01-LIP03. In another embodiment, the fusion protein is a LIP01-LIP03 protein containing a heterologous signal sequence at its N-terminus. In certain host cells (e.g., mammalian and yeast host cells), expression and/or secretion of LIP01-LIP03 can be increased through use of a heterologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokaryotic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by known methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., *Cell* 37:767 (1984), for instance.

Preferably, a LIP01-LIP03 fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers, which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). A LIP01-LIP03-encoding nucleic acid can be cloned into such an expression vector such that the fusion moiety is linked in-frame to the LIP01-LIP03 protein.

Functional Equivalents

The terms "functional equivalents" and "functional variants" are used interchangeably herein. Functional equivalents of LIP01-LIP03 DNA are isolated DNA fragments that encode a polypeptide that exhibits a particular function of the LIP01-LIP03 lipolytic enzyme as defined herein. A functional equivalent of a LIP01-LIP03 polypeptide according to the invention is a polypeptide that exhibits at least one function of a *Magnaporthe grisae* lipolytic enzyme as defined herein. Functional equivalents therefore also encompass biologically active fragments.

Functional protein or polypeptide equivalents may contain only conservative substitutions of one or more amino acids of SEQ ID NO: 5-14 or substitutions, insertions or deletions of non-essential amino acids. Accordingly, a non-essential amino acid is a residue that can be altered in SEQ ID NO: 5-14 without substantially altering the biological function. For example, amino acid residues that are conserved among the LIP01-LIP03 proteins of the present invention are predicted to be particularly unamenable to alteration. Furthermore, amino acids conserved among the LIP01-LIP03 proteins according to the present invention and other lipolytic enzyme are not likely to be amenable to alteration.

The term "conservative substitution" is intended to indicate a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding LIP01-LIP03 proteins that contain changes in amino acid residues that are not essential for a particular biological activity. Such LIP01-LIP03 proteins differ in amino acid sequence from SEQ ID NO: 2, SEQ ID NO: 3, SEQ ID NO: 4; SEQ ID NO: 5; SEQ ID NO: 6 yet retain at least one biological activity thereof. In one embodiment the isolated nucleic acid molecule comprises a nucleotide sequence encoding a protein, wherein the protein comprises a substantially homologous amino acid sequence of at least about 60%, preferably 65%, more preferably 70%, even more preferably 75%, 80%, 85%, 90%, 95%, 96%, 97%, 98%, 99% or more homologous to the amino acid sequence shown in SEQ ID NO: 5-14.

For example, guidance concerning how to make phenotypically silent amino acid substitutions is provided in Bowie, J. U. et al., Science 247:1306-1310 (1990) and the references cited therein. As the authors state, these studies have revealed that proteins are surprisingly tolerant of amino acid substitutions. The authors further indicate which changes are likely to be permissive at a certain position of the protein.

An isolated nucleic acid molecule encoding a LIP01-LIP03 protein homologous to the protein according to any one of SEQ ID NO: 5-7, SEQ ID NO: 8-9, SEQ ID NO: 10-14 respectively can be created by introducing one or more nucleotide substitutions, additions or deletions into the coding nucleotide sequences according to respectively any one of SEQ ID NO: 2-4 such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the LIP01-LIP03 protein. Orthologues of the LIP01-LIP03 protein are proteins that can be isolated from other strains or species and possess a similar or identical biological activity. Such orthologues can readily be identified as comprising an amino acid sequence that is substantially homologous to SEQ ID NO: 5-14.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Also, nucleic acids encoding other LIP01-LIP03 family members, which thus have a nucleotide sequence that differs from SEQ ID NO: 2-4 are within the scope of the invention. Moreover, nucleic acids encoding LIP01-LIP03 proteins from different species which can have a nucleotide sequence which differs from SEQ ID NO: 2-4 are within the scope of the invention.

Nucleic acid molecules corresponding to variants (e.g. natural allelic variants) and homologues of the LIP01-LIP03 DNA of the invention can be isolated based on their homology to the LIP01-LIP03 nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the LIP01-LIP03 sequence, the skilled person will recognise that changes can be introduced by mutation into the nucleotide sequences of SEQ ID NO: 2-4 thereby leading to changes in the amino acid sequence of the LIP01-LIP03 protein without substantially altering the function of the LIP01-LIP03 protein.

In another aspect of the invention, improved LIP01-LIP03 proteins are provided. Improved LIP01-LIP03 proteins are proteins wherein at least one biological activity is improved. Such proteins may be obtained by randomly introducing mutations along all or part of the LIP01-LIP03 coding sequence, such as by saturation mutagenesis, and the resulting mutants can be expressed recombinantly and screened for biological activity. For instance, the art provides for standard assays for measuring the enzymatic activity of lipolytic enzyme and thus improved proteins may easily be selected.

In a preferred embodiment the LIP01-LIP03 protein has an amino acid sequence according to SEQ ID NO: 5-7, SEQ ID NO: 8-9, SEQ ID NO: 10-14 respectively. In another embodiment, the LIP01-LIP03 polypeptide is substantially homologous to the amino acid sequence according to SEQ ID NO: 5-14 and retains at least one biological activity of a polypeptide according to SEQ ID NO: 5-14, yet differs in amino acid sequence due to natural variation or mutagenesis as described above.

In a further preferred embodiment, the LIP01-LIP03 protein has an amino acid sequence encoded by an isolated nucleic acid fragment capable of hybridising to a nucleic acid according to respectively any one of SEQ ID NO: 2-4, preferably under highly stringent hybridisation conditions.

Accordingly, the LIP01-LIP03 protein is preferably a protein which comprises an amino acid sequence at least about 60%, 65%, 70%, 75%, 80%, 85%, 90%, 95%, 96%, 97%, 98%, 99% or more homologous to the amino acid sequence shown in SEQ ID NO: 5-14 and retains at least one functional activity of the polypeptide according to SEQ ID NO: 5-14.

Functional equivalents of a protein according to the invention can also be identified e.g. by screening combinatorial libraries of mutants, e.g. truncation mutants, of the protein of the invention for lipolytic enzyme activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g. for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations of truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3): 327-331).

In addition to the LIP01-LIP03 gene sequence shown in SEQ ID NO: 2-4 respectively, it will be apparent for the person skilled in the art that DNA sequence polymorphisms may exist in within a given population, which may lead to changes in the amino acid sequence of the LIP01-LIP03 protein. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention irrespective of whether they encode functional or non-functional polypeptides can be used as hybridization probes or polymerase chain reaction (PCR) primers. Uses of the nucleic acid molecules of the present invention that do not encode a polypeptide having a LIP01-LIP03 activity include, inter alia, (1) isolating the gene encoding the LIP01-LIP03 protein, or allelic variants thereof from a cDNA library e.g. from other organisms than *Magnaporthe grisae*; (2) in situ hybridization (e.g. FISH) to metaphase chromosomal spreads to provide precise chromosomal location of the LIP01-LIP03 gene as described in Verma et al., Human Chromosomes: a Manual of Basic Techniques, Pergamon Press, New York (1988); (3) Northern blot analysis for detecting expression of LIP01-LIP03 mRNA in specific tissues and/or cells and 4) probes and primers that can be used as a diagnostic tool to analyse the presence of a nucleic acid hybridisable to the LIP01-LIP03 probe in a given biological (e.g. tissue) sample.

Also encompassed by the invention is a method of obtaining a functional equivalent of a LIP01-LIP03 gene. Such a method entails obtaining a labelled probe that includes an isolated nucleic acid which encodes all or a portion of the protein sequence according to SEQ ID NO: 5-14 or a variant of any of them; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the LIP01-LIP03 gene.

In one embodiment, a LIP01-LIP03 nucleic acid of the invention is at least 85%, 90%, 91%, 92%, 93%, 94%, 95%, 96%, 97%, 98%, 99%, or more homologous to a nucleic acid sequence shown in respectively any one of SEQ ID NO: 2-4 or the complement thereof.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Magnaporthe grisae* or *Aspergillus* species such as *Aspergillus niger* or *oryzae*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, a stably transfected cell line can produce the polypeptides according to the invention. A number of vectors suitable for stable transfection of mammalian cells are available to the public, methods for constructing such cell lines are also publicly known, e.g., in Ausubel et al. (supra).

Use of LIP01-LIP03 Lipolytic Enzyme in Industrial Processes

Surprisingly, the lipolytic enzyme according to the invention is not restricted to hydrolysis of merely one specific substrate, but is capable of different types of lipolytic activity, being phospholipase, lipase and galactolipase activity. The lipolytic enzyme according to the invention may show these activities at the same time or may have a narrow specificity with one single activity and little or no other activity, or it may have a broader specificity with one predominant activity and less other activities, depending on the composition of the dough, time of reaction, pH, temperature, water-content.

Due to its diversity, the lipolytic enzyme according to the invention may be used in a manifold of industrial applications, including for the production of digalactosylmonoglyceride from a digalactosyldiglyceride containing source or the modification of phospholipid emulsifiers. An example of a phospholipid emulsifier is lecithin, which is a mixture of both polar and neutral lipids in which the content of polar lipids is at least 60%. Phospholipid emulsifiers have many food and non-food applications, for example egg-lecithin is used as an emulsifier in for example dairy products, specifically mayonnaise, dressings, pastry, etc., soya lecithin for example, is for example used as an emulsifier in (low calorie) sauces, bread, margarine, cosmetics etc, other lecithins are used in for example chocolates, calf feed. Modification of phospholipid emulsifiers by the lipolytic enzyme according to the invention may cause an increased emulsification of the oil/water mixture. Modification of phospholipid emulsifiers by the lipolytic enzyme according to the invention may increase the stability of the emulsions resulting from the addition of the modified phospholipid emulsifiers for a wider or different pH and/or temperature range. Modification of phospholipid emulsifiers by the lipolytic enzyme according to the invention may increase the stability of the emulsions, resulting from the addition of modified phospholipid emulsifiers, in the presence of $Ca^{2+}$ or $Mg^{2+}$ ions.

Another example of industrial application of the lipolytic enzyme according to the invention is that it can be used for the degumming of vegetable oils in the processing of these oils. In a typical degumming process, lecithins are removed from vegetable oils, for example soy oils, rapeseed (canola) oils, linseed oils, sunflower oils, to increase among others the stability of the vegetable oil, by washing the oil phase with water, wherein mixing of the water and oil under high shear conditions forces the bulk of the lecithins into the aqueous phase, which is subsequently removed in a separator. In this so-called water degumming phase, only the rapidly hydratable phospholipids are readily removed, for example phosphatidylcholine, phosphatidylinositol and phosphatidylethanolamine. The non-hydratable phospholipids/phosphatides, mostly the phospholipids, which consist of up to 50% of magnesium and/or calcium salts cannot readily be removed in the water degumming step. Exposure of the non-hydratable phospholipids/phosphatides to the lipolytic enzyme according to the invention makes these phospholipids more soluble in water and therefore easier to extract in a water degumming phase.

Another example of industrial application of the lipolytic enzyme according to the invention is to remove the precipitate that occurs during the saccharification (with the aid of α-amylase and glucoamylase) of wheat gluten or wheat starch to produce glucose syrups. The removal of the precipitate considerably speeds up the subsequent filtration of the resulting glucose syrups.

Yet another example of an industrial application of the lipolytic enzyme according to the invention in food is its use in baking applications to improve dough or baked product quality.

Surprisingly, the lipase according to the invention shows at least one of the following properties in situ when used in dough (and also in the other mentioned industrial processes):
 a relatively low activity towards apolar lipids
 a relatively high activity towards polar diacyl-lipids, at least towards diacyl galactolipids
 a relatively low activity towards polar monoacyl compounds.

For example, the enzyme according to the invention can show in situ a relatively low lysophospholipase activity and a relatively low lipase activity. These unexpected properties are all found to be extremely advantageous when used as a replacer of chemical emulsifiers in dough.

Several types of phospholipase activity can be distinguished which hydrolyse the ester bond(s) that link the fatty acyl moieties to the glycerol backbone:
 Phospholipase A1 (EC 3.1.1.32) and A2 (EC 3.1.1.4) catalyse the deacylation of one fatty acyl group in the sn-1 and sn-2 positions respectively, from a diacylglycerophospholipid to produce a lysophospholipid. This is a desirable activity for emulsifier replacement.
 Lysophospholipase (EC 3.1.1.5—also called phospholipase B by the Nomenclature Committee of the International Union of Biochemistry and Molecular Biology (Enzyme Nomenclature, Academic Press, New York, 1992)) catalyses the hydrolysis of the remaining fatty acyl group in a lysophospholipid. A phospholipase B has been reported from *Penicillium notatum* (Saito et al., 1991, Methods in Enzymology 197:446-456), which catalyses the deacylation of both fatty acids from a diacylglycerophospholipid and intrinsically possesses lysophospholipase activity. For emulsifier replacement lysophospholipase activity is less desirable, since this would result in deletion of the combination of a polar head and apolar tail, disabling the resulting product to influence surface properties. Surprisingly was shown that the lipase according to the invention, shows relatively low lysophospholipase activity in the dough.

Wheat flour contains approximately 2.2-2.9% lipids. The flour lipids can be divided into starch lipids (0.8-0.9%) and non-starch lipids (1.4-2.0%). Whereas the starch lipids consist mainly of polar lysophospholipids, the non-starch lipids consist of about 40% neutral triglycerides and 40% polar phospho- and glycolipids. For optimisation of the flour lipids fraction the lipase according to the invention is capable of hydrolysation of the polar lipids, being the phospholipids and glycolipids, more specifically the galactolipids in situ in the dough by adding the lipase according to the invention.

WO04/104193 discloses the use of a phospholipase C from *Magnaporthe grisae* in baking applications. However, phospholipase C activity is not desirable for an enzyme to be used as a replacement for chemical emulsifiers, since this does not yield sufficient surface-active compounds. Furthermore, the phospholipase C disclosed in WO04/104193 non-homologous to SEQ ID NO: 3, 4 or 5.

WO 98/45453 discloses a polypeptide having lipase activity derivable from *Aspergillus tubigensis* which is also showing hydrolytic activity on digalactosyldiglyceride. This enzyme, however, suffers from a relatively low specific activity on galactosyldiglycerides and a relatively high activity on triglycerides in situ in bread (example 10), which makes this enzyme not suitable to be used as full-replacement for chemical emulsifiers.

Baking enzymes may be used in a manifold of baked products. The term "baked products" is herein defined as to comprise bread products such as tin bread, loaves of bread, French bread as well as rolls, cakes, pies, muffins, yeast raised and cake doughnuts and the like.

The lipolytic enzyme according to the invention can for example be used in baked products. Baked products such as bread are prepared from a dough which is usually made from the basic ingredients (wheat) flour, water and optionally salt. Depending on the baked products, other ingredients added may be sugars, flavours etceteras. For leavened products, primarily baker's yeast is used next to chemical leavening systems such as a combination of an acid (generating compound) and bicarbonate.

Yeast, enzymes and chemical additives are generally added separately to the dough.

Enzymes may be added in a dry, e.g. granulated form or in liquid form. The chemical additives are in most cases added in powder form. Also, processing aid compositions which are tailored to specific baking applications, may be composed of a dedicated mixture of chemical additives and enzyme.

The preparation of a dough from the ingredients and processing aids described above is well known in the art and comprises mixing of said ingredients and processing aids and one or more moulding and fermentation steps.

The preparation of baked products from such doughs is also well known in the art and may comprise molding and shaping and further fermentation of the dough followed by baking at required temperatures and baking times.

The present invention addresses at least one if not all of the above problems.

The invention also relates to the use of the lipolytic enzyme according to the invention in a number of industrial processes. Despite the long-term experience obtained with these processes, the lipolytic enzyme according to the invention features a number of significant advantages over the enzymes currently used. Depending on the specific application, these advantages can include aspects like lower production costs, higher specificity towards the substrate, less antigenic, less undesirable side activities, higher yields when produced in a suitable microorganism, more suitable pH and temperature ranges, better tastes of the final product as well as food grade and kosher aspects.

The present invention also relates to methods for preparing a dough or a baked product comprising incorporating into the dough an effective amount of a lipolytic enzyme of the present invention which improves one or more properties of the dough or the baked product obtained from the dough relative to a dough or a baked product in which the polypeptide is not incorporated.

The phrase "incorporating into the dough" is defined herein as adding the lipolytic enzyme according to the invention to the dough, any ingredient from which the dough is to be made, and/or any mixture of dough ingredients form which the dough is to be made. In other words, the lipolytic enzyme according to the invention may be added in any step of the dough preparation and may be added in one, two or more steps. The lipolytic enzyme according to the invention is added to the ingredients of a dough that is kneaded and baked to make the baked product using methods well known in the art. See, for example, U.S. Pat. No. 4,567,046, EP-A-426,211, JP-A-60-78529, JP-A-62-111629, and JP-A-63-258528.

The term "effective amount" is defined herein as an amount of the lipolytic enzyme according to the invention that is sufficient for providing a measurable effect on at least one property of interest of the dough and/or baked product.

The term "improved property" is defined herein as any property of a dough and/or a product obtained from the dough, particularly a baked product, which is improved by the action of the lipolytic enzyme according to the invention relative to a dough or product in which the lipolytic enzyme according to the invention is not incorporated. The improved property may include, but is not limited to, increased strength of the dough, increased elasticity of the dough, increased stability of the dough, reduced stickiness of the dough, improved extensibility of the dough, improved machineability of the dough, increased volume of the baked product, improved flavour of the baked product, improved crumb structure of the baked product, improved crumb softness of the baked product, reduced blistering of the baked product and/or improved anti-staling of the baked product.

The improved property may be determined by comparison of a dough and/or a baked product prepared with and without addition of a polypeptide of the present invention in accordance with the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume and is evaluated by the ratio of height:width of a cross section of a loaf after normal and/or extended proof.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g., TAXT2) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic.

The term "increased volume of the baked product" is measured as the volume of a given loaf of bread determined by an automated bread volume analyser (e.g. BVM-3, TexVol Instruments AB, Viken, Sweden), using ultrasound or laser detection as known in the art.

The term "reduced blistering of the baked product" is defined herein as a visually determined reduction of blistering on the crust of the baked bread.

The term "improved crumb structure of the baked product" is defined herein as the property of a baked product with finer cells and/or thinner cell walls in the crumb and/or more uniform/homogenous distribution of cells in the crumb and is usually evaluated visually by the baker or by digital image analysis as known in the art (e.g. C-cell, Calibre Control International Ltd, Appleton, Warrington, UK).

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved anti-staling of the baked product" is defined herein as the properties of a baked product that have a reduced rate of deterioration of quality parameters, e.g., softness and/or elasticity, during storage.

The term "dough" is defined herein as a mixture of flour and other ingredients firm enough to knead or roll. The dough may be fresh, frozen, prepared, or pre-baked. The preparation of frozen dough is described by Kulp and Lorenz in Frozen and Refrigerated Doughs and Batters.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, noodles (boiled or (stir-)fried), pita bread, tortillas, tacos, cakes, pancakes, biscuits, cookies, doughnuts, bagels, pie crusts, steamed bread, and crisp bread, and the like.

Lipolytic enzyme of the present invention and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme such described in WO01/11974 and WO02/26044. Granulates and agglomerated powders may be prepared by conventional methods, e.g., by spraying the lipolytic enzyme according to the invention onto a carrier in a fluid-bed granulator. The carrier may consist of particulate cores having a suitable particle size. The carrier may be soluble or insoluble, e.g., a salt (such as NaCl or sodium sulphate), sugar (such as sucrose or lactose), sugar alcohol (such as sorbitol), starch, rice, corn grits, or soy. The lipolytic enzyme according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

The lipolytic enzyme according to the invention may also be incorporated in yeast comprising compositions such as disclosed in EP-A-0619947, EP-A-0659344 and WO02/49441.

For inclusion in pre-mixes of flour it is advantageous that the polypeptide according to the invention is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase,—such as an alpha-amylase (useful for providing sugars fermentable by yeast and retarding staling), beta-amylase, maltogenic amylase or non-maltogenic amylase-, cyclodextrin glucanotransferase, peptidase, in particular, an exopeptidase (useful in flavour enhancement), transglutaminase, lipase (useful for the modification of lipids present in the dough or dough constituents so as to soften the dough), galactolipase, phospholipase, cellulase, hemicellulase, in particular a pentosanase such as xylanase (useful for the partial hydrolysis of pentosans, more specifically arabinoxylan, which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an glucose oxidase, hexose oxidase, aldose oxidase, pyranose oxidase, lipoxygenase or L-amino acid oxidase (useful in improving dough consistency).

When one or more additional enzyme activities are to be added in accordance with the methods of the present invention, these activities may be added separately or together with the polypeptide according to the invention, optionally as constituent(s) of the bread-improving and/or dough-improving composition. The other enzyme activities may be any of the enzymes described above and may be dosed in accordance with established baking practices.

The present invention also relates to methods for preparing a baked product comprising baking a dough obtained by a method of the present invention to produce a baked product. The baking of the dough to produce a baked product may be performed using methods well known in the art.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide of the present invention. The term "pre-mix" is defined herein to be understood in its conventional meaning, i.e., as a mix of baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide of the present invention. The baking additive preferably has a narrow particle size distribution with more than 95% (by weight) of the particles in the range from 25 to 500 μm.

In dough and bread making the present invention may be used in combination with the processing aids defined hereinbefore such as the chemical processing aids like oxidants (e.g. ascorbic acid), reducing agents (e.g. L-cysteine), and/or emulsifiers (e.g. DATEM, SSL and/or CSL) and/or enzymatic processing aids such as oxidoreductases (e.g. glucose oxidase), polysaccharide modifying enzymes (e.g. α-amylase, hemicellulase, branching enzymes, etc.) and/or protein modifying enzymes (endoprotease, exoprotease, branching enzymes, etc.).

The above-mentioned industrial applications of the lipolytic enzyme according to the invention comprise only a few examples and this listing is not meant to be restrictive.

The LIP01-LIP03 lipolytic enzyme may conveniently be produced in microorganisms. In the above processes, it is advantageous to use lipolytic enzyme that are obtained by recombinant DNA techniques. Such recombinant enzymes have a number of advantages over their traditionally purified counterparts. Recombinant enzymes may be produced at a low cost price, high yield, free from contaminating agents like bacteria or viruses but also free from bacterial toxins or contaminating other enzyme activities.

Hereafter the invention is illustrated by the following non-limiting examples.

EXAMPLES

Example 1

Fermentation of *Aspergillus niger*

The lipolytic enzymes encoded by the nucleotide sequences SEQ ID NO:2, SEQ ID NO:3 and SEQ ID NO:4 as provided herein were obtained by constructing expression plasmids containing the DNA sequences, transforming an *A. niger* strain with such plasmid and growing the *Aspergillus niger* strains in the following way.

Fresh spores ($10^6$-$10^7$) of *A. niger* strains were inoculated in 20 ml CSL-medium (100 ml flask, baffle) and grown for 20-24 hours at 34° C. and 170 rpm. After inoculation of 5-10 ml CSL pre-culture in 100 ml CSM medium (500 ml flask, baffle) the strains were fermented at 34° C. and 170 rpm for 3-5 days.

Cell-free supernatants were obtained by centrifugation in 50 ml Greiner tubes (30 minutes, 5000 rpm). The supernatants were pre-filtered over a GF/A Whatman Glass microfiber filter (150 mm Æ) to remove the larger particles, adjusted to pH 5 with 4 N KOH (if necessary) and sterile filtrated over a 0.2 μm (bottle-top) filter with suction to remove the fungal material. The supernatant were stored at 4° C. (or −20° C.).

The CSL medium consisted of (in amount per liter): 100 g Corn Steep Solids (Roquette), 1 g NaH$_2$PO4*H$_2$O, 0.5 g MgSO$_4$*7H$_2$O, 10 g glucose*H$_2$O and 0.25 g Basildon (antifoam). The ingredients were dissolved in demi-water and the pH was adjusted to pH 5.8 with NaOH or H$_2$SO$_4$; 100 ml flasks with baffle and foam ball were filled with 20 ml fermentation broth and sterilized for 20 minutes at 120° C. after which 200 μl of a solution containing 5000 IU/ml penicillin and 5 mg/ml Streptomycin was added to each flask after cooling to room temperature.

The CSM medium consisted of (in amount per liter): 150 g maltose*H2O, 60 g Soytone (pepton), 1 g NaH$_2$PO4*H$_2$O, 15 g MgSO$_4$*7H$_2$O, 0.08 g Tween 80, 0.02 g Basildon (antifoam), 20 g MES, 1 g L-arginine. The ingredients were dissolved in demi-water and the pH was adjusted to pH 6.2 with NaOH or H$_2$SO$_4$; 500 ml flasks with baffle and foam ball were filled with 100 ml fermentation broth and sterilized for 20 minutes at 120° C. after which 1 ml of a solution containing 5000 IU/ml penicillin and 5 mg/ml Streptomycin was added to each flask after cooling to room temperature.

Example 2

Purification of the Lipolytic Enzyme of the Invention

Step 1—Preparation of Ultrafiltrates

The supernatants of the cultures, as obtained in Example 1, were ultrafiltrated to remove the low molecular contaminations that could interfere with the enzymatic activity determinations and the baking tests. Ultrafiltration of 30 ml supernatant was performed in a Millipore Labscale TFF system equipped with a filter with a 10 kDa cut-off.

Depending on their colour, the samples were washed 3-5 times with 40 ml volumes of cold 100 mM phosphate buffer pH 6.0 including 0.5 mM CaCl$_2$. The final volume of the enzyme solution was 30 ml and is further referred to as "ultrafiltrate".

Total protein content of the samples was determined using the Bradford method (The Protein Protocols Handbook, 2$^{nd}$ edition, Edited by J. M. Walker, Humana Press Inc, Totowa 2002, p 15-21).

Step 2—Determination of the Lipolytic Enzyme Concentration by A280 and HPSEC

The concentration of the lypolytic enzyme in the ultrafiltrate was calculated from the extinction at 280 nm (A280) attributable to the lipolytic enzyme and the calculated molecular extinction coefficient of the lipolytic enzyme. Measurement of the A280 was performed in an Uvikon XL Secomam spectrophotometer (Beun de Ronde, Abcoude, The Netherlands).

The molecular extinction coefficient of an enzyme can be calculated from the number of tyrosine, tryptophan and cysteïne residues per enzyme molecule (S. C. Gill and P. H. von Hippel, Anal. Biochem. 182, 319-326 (1989)). The molecular extinction coefficient of these amino acids are 1280, 5690 and 120 M$^{-1}$·cm$^{-1}$ respectively. The number of tyrosine, tryptophan and cysteïne residues in the lipolytic enzyme of the invention can be deduced from the protein sequences selected from the group consisting of SEQ ID NO: 5-14. The calculated extinction coefficients are shown in Table 1.

TABLE 1

Calculated extincion coefficients and M.W. of the LIP01-LIP03 enzymes

| Enzyme | SEQ ID NO: | # amino acids Trp | Tyr | Cys | Calculated M.W. (Da) | Calculated extinction coefficient At 280 nm M$^{-1}$·cm$^{-1}$ | (1 mg/ml)$^{-1}$·cm$^{-1}$ |
|---|---|---|---|---|---|---|---|
| LIP 01 | 5 | 5 | 17 | 9 | 37.8 | 52830 | 1.4 |
|  | 6 | 5 | 16 | 8 | 34.2 | 51340 | 1.5 |
|  | 7 | 5 | 15 | 8 | 29.9 | 49850 | 1.7 |
| LIP 02 | 8 | 5 | 17 | 9 | 37.8 | 50690 | 1.3 |
|  | 9 | 5 | 15 | 8 | 29.9 | 48130 | 1.3 |
| LIP 03 | 10 | 6 | 17 | 9 | 37.7 | 56380 | 1.5 |
|  | 11 | 6 | 15 | 8 | 29.9 | 53820 | 1.4 |
|  | 12 | 5 | 15 | 8 | 29.7 | 48130 | 1.3 |
|  | 13 | 5 | 15 | 8 | 29.6 | 48130 | 1.3 |
|  | 14 | 6 | 16 | 8 | 34.2 | 55100 | 1.5 |

The extinction of the ultrafiltrate at 280 nm (A280) that is attributable to the lipolytic enzyme depends on the purity of the enzyme sample. This purity was determined using HPSEC (High Performance Size Exclusion Chromatography) with a TSK SW-XL column (300*7.8 mm; MW range 10-300 kDa). The elution buffer consisted of 25 mM sodium phosphate buffer pH 6.0 and was used at a flow of 1 ml/min. Samples of 5-100 μl were injected. The absorbance at 280 nm was measured.

The A280 in the ultrafiltrate attributable to the lipolytic enzyme of the invention was obtained from the ratio of the peak surface of the respective lipolytic enzyme peak in the chromatogram and the total surface of the peaks absorbing at 280 nm. The lipolytic enzyme concentration in the ultrafiltrate was then calculated by multiplying the A280 of the ultrafiltrate by the ratio described above and divided by the calculated extinction coefficient (1 mg/ml solution—Table 1 most right column) for the lipolytic enzyme.

Example 3

Activity Measurements

The ultrafiltrates obtained in Example 2 can be subjected to the following enzyme activity measurements in order to establish the specificity of the lipolytic enzyme:
Lipase
Phospholipase A$_1$ or A$_2$
Lysophospholipase
Galactolipase activity Lipase activity was determined spectrophotometrically by using the chromogenic substrate p-nitrophenyl palmitate (pNPP). In this assay the chromogenic substrate p-nitrophenyl palmitate (pNPP) is dissolved in 2-propanol and suspended in phosphate buffer pH 7.4 in the presence of 0.1% gum Arabic and 0.25% sodium deoxycholate. The lipase is incubated with this substrate solution at 37° C. and the formed p-nitrophenyl (pNP) is measured for 2.6 minutes at 405 nm. This assay can also be applied at different pH values in order to determine pH dependence of a lipase. It should be understood that at different pH values different buffers might be required or that different detergents might be necessary to emulsify the substrate. For example at pH=4 100 mM Acetate buffer with 1.0% Triton X-100 is used. One lipase unit is defined as the amount of enzyme that liberates 1 micromole of p-nitrophenol per minute at the reaction conditions stated. It should be understood that it is not uncommon practice in routine analysis to use standard calibration enzyme solutions with known activity determined in a different assay to correlate activity a given assay with units as would be determined in the calibration assay.

Alternatively, lipase activity can be determined by using 2,3-mercapto-1-propanol-tributyrate (TBDMP) as a substrate. Lipase hydrolyses the thioester bond(s) of TBDMP thereby liberating butanoic acid and 2,3-mercapto-1-propanol-dibutyrate, 2,3-mercapto-1-propanol-monobutyrate or 2,3-mercapto-1-propanol. The liberated thiol groups are titrated in a subsequent reaction with 4,4,-dithiodipyridine (DTDP) forming 4-thiopyridone. The latter is in a tautomeric equilibrium with 4-mercapthopyridine which absorbs at 334 nm. The reaction is carried out in 0.1 M acetate buffer pH 5.0 containing 0.2% Triton-X100, 0.65 mM TBDMP and 0.2 mM DTDP at 37° C. One lipase unit is defined as the amount of enzyme that liberates 1 micromole of 4-thiopyridone per minute at the reaction conditions stated.

Phospholipase A activity was determined spectrophotometrically by using 1,2-dimercaptodioctanoyl-phosphatidylcholine as a substrate. Phospholipase A hydrolyses the thioester bond at the 1 position (PLA1) or at the 2 position (PLA2) thereby liberating octamoic acid and 1,2-dimercapto-mono-octanoyl-phosphatidylcholine or 1,2-dimercapto-phosphatidylcholine. The liberated thiol groups are titrated in a subsequent reaction with 4,4'-dithiopyridine to form 4-thiopyridone. The latter is in tautomeric equilibrium with 4-mercaptopyridine that absorbs at 334 nm. The reaction is carried out in 0.1 M acetate buffer pH 4.0+0.2% Triton-X100 at 37° C. One phospholipase A unit (APLU) is defined as the amount of enzyme that liberates 1 micromole of 4-thiopyridone per minute at the reaction conditions stated.

Lysophospholipase activity can be determined with $^{31}$P-NMR spectroscopy by using lysophosphatidyl-choline as a substrate. Lysophospholipase hydrolyses the ester bond thereby liberating the fatty acid from the glycerol moiety. The so-formed glycerolphosphocholine is quantified using NMR. The reaction is carried out in 50 mM acetic acid buffer pH 4.5 further containing 1 mg/ml lysophosphatidylcholine and 5 mM $CaCl_2$ for 30 minutes at 55° C. One lysophospholipase unit (LPC) is defined as the amount of enzyme that forms 1 micromole of glycerolphosphocholine per minute at the reaction conditions stated.

Galactolipase activity was determined with H-NMR spectroscopy by using digalactosyldiglyceride as a substrate, according to the method described by Hirayama and Matsuda (1972) Agric. Biol. Chem. 36, 1831. Galactolipase hydrolyses the ester bond between the fatty acids and the glycerol backbone thereby liberating one or both fatty acids. The reaction is carried out in 50 mM acetic acid buffer pH 4.5 further containing 4 mM $CaCl_2$, 0.2% Triton X-100 and 1 mg/ml digalactosyldiglyceride (Lipid Products) for 30 minutes at 30° C. One galactolipase unit is defined as the amount of enzyme that forms 1 micromole of fatty acid per minute at the reaction conditions stated.

In addition to spectrophotometric measurement lipase activity can also be determined using titrimetric measurement. For example the esterase activity of a lipolytic enzyme may be measured on tributyrin as a substrate according to Food Chemical Codex, Forth Edition, National Academy Press, 1996, p 803. Lipase activity is preferably determined using triacylglyceride substrates with longer fatty acids, e.g. palmitic acid, stearic acid, oleic acid, linoleic acid, linolenic acid. Often olive oil is applied in such assays. Phospholipase, lysophospholipase and galactolipase can in principle also be analysed with titrimetric methods.

In addition to the lipolytic activities mentioned, non-lipolytic side activities might also be present in the samples, e.g. alpha-amylase activity. The activity of the fungal alpha-amylase can be measured using Phadebas Amylase test tablets (Pharmacia). Phadebas tablets contain a water insoluble starch substrate and a blue dye, bound by cross-linking to the substrate. The substrate is hydrolysed by fungal amylase, releasing dyed soluble maltodextrines that go into solution. A calibration curve was prepared with a solution containing a reference fungal alpha amylase activity.

From the reference and unknown samples appropriate dilutions were prepared in 50 mM malic acid buffer pH 5.5. Samples of 5 ml were incubated with 30° C. for 5 minutes, a Phadebas tablet was added and after 15 minutes the reaction was stopped by the addition of 1.0 ml 0.5 N sodium hydroxide. The mixtures were allowed to cool down to room temperature for 5 minutes after which 4.0 ml water was added, shaken by hand and after 15 minutes the samples were centrifuged at 4700 rpm for 10 minutes. The extinction of the top layers was measured at 620 nm. The OD 620 nm is a measure for fungal alpha amylase activity;

One fungal amylase unit (FAU) is defined herein as the amount of enzyme that converts 1 gram of starch (100% dry matter) per hour into a product having a transmission at 620 nm after reaction with a iodine solution of known strength at the reaction conditions stated.

In addition to the activities mentioned, minor activities of glucoamylase, protease and xylanase were also present, however in such low amounts that these enzymes did not interfere in the baking experiments described in the examples below. The cell-free ultrafiltrates obtained in Example 1 were subjected to the lipase, phospholipase and galactolipase assays as summarized in Table 2.

TABLE 2

Lipolytic enzyme activities in the cell-free clarified filtrates as prepared in Example 1 (lipase activity was determined at pH 5).

| Lipolytic enzyme | Lipase | Phospholipase A | Galactolipase |
|---|---|---|---|
| LIP01 | 355 | 72466 | 140 |
| LIP02 | 338 | 130546 | 320 |
| LIP03 | 14 | 841 | 813 |

It should be noted that in the various assays only a single substrate is present, and that the activity numbers do not predict actual activities in mixtures of various lipoidic substrates or in industrial applications such as dough. In such case affinity or specificity for substrates to become important.

Enzymatic Characterisation

SDS-PAGE molecular weight estimation was performed with NuPage 4-12% MES Simply Blue Safe Stain on the ultrafiltrate samples. For LIP01 the estimated Mw=33 kD. For LIP02 the estimated Mw=33 kD. For LIP03 two major bans were observed corresponding to Mw=33 kD and Mw=41 kD.

Isoelectric Focusing Experiment.

Calculated pI for mature LIP01 275 amino acid protein: 5.

Calculated pI for translated gene of LIP01: 5.4

Calculated pI for translated gene of LIP02: 5.4. Calculated pI for mature 276 amino acid LIP02 protein: 5.5. The pI of LIP02 was determined experimentally using gel electroforesis and an ampholite range 3-10. The IEF experiment shows multiple bands in the range 4-5 with main bands at pI=4.7 and pI=4.3.

Calculated pI for mature 276 amino acid LIP03 protein: 5.1 (using SEQ1)
Calculated pI for translated LIP03 gene of 348 amino acids: 5.1 (using SEQ10)
Calculated pI for translated LIP03 gene of 314 amino acids: 4.8 (using SEQ14)
Isoelectric focussing of the LIP03 lipase produced in *A. niger* showed multiple bands in the range pI=4 up to pI=5.0 with major bands around pI=4.7 and pI=4.4.

Determination of Glycosylation.

Glycosylation might affect the observed molecular weight on PAA-SDS gels. Usually the molecular weight is overestimated. In order to verify whether the LIP01-03 protein is glycosylated and to effectively determine the protein molecular weight, the protein sample was treated with PNGASE-F glycosydase in order to deglycosylate the protein. Subsequently both treated and untreated sample were subjected to PAA-SDS geleelectroforesis. Two potential N-glycosylation sites are present in the mature 275 LIP01 amino acid protein: 126 NLTF and 264 NYTF. One potential glycosylation site is present in the mature 276 amino acid LIP02 protein: 264 NYTF. The untreated LIP02 shows a band around 33 kD while after deglycosylation a band is observed around 30 kD. One potential N-glycosylation site is present in the mature 276 amino acid protein: 264 NYTF. The untreated LIP03 shows two bands, one around 33 kD and one around 41 kD. After deglycosylation again two bands are observed, one around 30 kD and one around 38 kD. These results suggest two forms of LIP03 occur that are both glycosylated to the same extent.

Characterisation and handling of glycoproteins is extensively described in The Protein Protocols Handbook, 2$^{nd}$ edition, Edited by J. M. Walker, Humana Press Inc, Totowa 2002, chapter VI.

The intact mass of the produced lipolytic enzyme can be determined by using LC/MS, according to the following protocol:

| LC | |
|---|---|
| Eluentia | A: 0.1% TFA in MQ B: 0.1% TFA in ACN |
| Gradient | Start at 0% B, increasing to 80% B in 15 minutes and kept here for 15 minutes |
| Column | Prosphere C4 300 μm * 50 mm |
| Flow | 2 μl/min |
| Injection volume | 5 μl/min |
| MS | |
| Instrument | Qtof-2 (SM06) |
| LC/MS | Nano ESI/pos |
| MS | Full scan 500-3000 amu |

The protein samples were desalted by filtering over a 10 kDa centrifugal device filter (Pall) by centrifugation at 13000 rpm for 15 minutes at 4° C. Deglycosylation was done by enzymatic deglycosylation with peptide-N-glycosidase F (PNGase, Roche Diagnostics GmbH, Manheim Germany). The filtrate of LIP01-LIP03 was dissolved in 100 mM ammoniumbicarbonate and was denatured by incubation at 95° C. for ten minutes. PNGASE-F (20 units) was added to the samples and deglycosylation was performed by incubation at 37° C. overnight. After deglycosylation the samples were again filtered over a 10 kDa centrifugal device filter (Pall) by centrifugation at 13000 rpm for 15 minutes to get rid of the sugars. The filtrates from the desalting and the filtrates after deglycosylation were dissolved in 50/50/5 AcN/MQ/FA to a final concentration of approximately 1 mg/mL. The samples were injected on the QTOFII mass spectrometer by direct infusion and the intact masses were calculated using the MaxEnt1 logarithm in the Masslynx software (version 4 sp2, Waters).

For LIP02 a molecular weight of 32265 was calculated by deconvolution of the MS spectra of intact LIP02 sample. For the deglycosylated LIP02 an intact mass was calculated of 29905 Da, which corresponds to residues 35-310 of the theoretical amino acid sequence (SEQ NO 2). The difference in intact mass observed before and after deglycosylation corresponds probably to 12 mannose groups and 2 GlcNAC groups attached to the protein.

For the deglycosylated LIP03 more than one intact mass was observed. Both intact masses of LIP03 with and without the C-terminal peptide were calculated, MW=29835 (SEQ3, 35-310) and MW=34100 (SEQ6, 35-348) respectively. In addition the C-terminus of the MW=29835 (SEQ3) fragment is ragged, since the masses of residue 35-309 (SEQ4) and 35-308 (SEQ5) were also observed, where especially residue 35-309 is quite abundant compared to residue 35-310. This indicates that C-terminal cleavage of LIP03 is not completely specific.

pH Optimum

The pH optimum dependence of the lipolytic enzyme can be determined by carrying out an assay that measures certain type of lipolytic activity at different pH values. The pH at which maximal activity is observed is the pH optimum of the particular enzyme. As the pH optimum might depend on the type of substrate and the applied assay conditions, it should be reestablished when different substrates are used or when assay conditions drastically change.

Temperature Optimum

The temperature optimum of the lipolytic enzyme is determined by carrying out a given assay at different temperatures. By plotting the activity as a function of the temperature the temperature optimum of the enzyme can be determined.

Thermostability

The thermostability of the lipolytic enzyme can be determined by means of Differential Scanning Calorimetry (DSC). As an alternative the thermostability may be analyzed by T50 determination. The T50 is defined as the temperature at which 50% of the activity is lost upon heating the lipolytic enzyme for 20 minutes at given conditions.

The storage stability can be determined by storing the lipolytic enzyme under certain conditions at a certain temperature. After different time spans samples are taken and the residual activity in these samples is determined under standard assay conditions.

Example 4

Baking Experiment—Mini-Batard

Mini-batards were baked from 150 gram dough pieces obtained by mixing 200 g flour (Kolibri™), 4.6 g compressed yeast, 4 g salt, 68 ppm ascorbic acid, 1 ppm Bakezyme® P500 (fungal alpha-amylase), 5 ppm Bakezyme® HSP6000 (fungal hemicellulase), and 114 ml water. After mixing for 6 minutes and 15 seconds in a pin mixer, the dough was divided into two pieces of 150 g, rounded and proofed for 25 minutes at ambient temperature and relative humidity of 90%. The dough pieces were then moulded and shaped and proofed for 100 minutes at 32° C. and 85% relative humidity. The fully proofed dough pieces were incised and baked in an oven at 240° C. for 20 minutes with initial steam addition.

The various effects of the lipolytic enzymes LIP01-LIP03 at different doses were compared to a blank, a loaf containing no extra additions, and a control loaf containing 0.3%

DATEM (Panodan® 80CP). The loaf volume was determined by an automated bread volume analyser (BVM-3, TexVol Instruments AB, Viken, Sweden) after cooling down of the loaves. The other effects were evaluated by an experienced baker according to the scales depicted in Table 3.

TABLE 3

Scores for effects observed in mini-batard

| Effect | Score | | | | |
|---|---|---|---|---|---|
| | 1 | 2 | 3 | 4 | 5 |
| Oven spring | incision closed completely | incision closed partially | Control bread | completely open incision | completely open incision; teared |
| Dough Stability | Flat | medium | Control bread | height/width ratio better than (3) | height/width ratio better than (3), spherical cross-section |
| Crumb structure | Poor | not uniform | Control bread | good | excellent |

TABLE 4

Baking performance of the lipolytic enzyme LIP01 at different doses (mg protein per kg flour (determined according to Bradford))

| | Control (DATEM) | Blank (0) | 0.6 | 1 | 2.4 | 3.8 |
|---|---|---|---|---|---|---|
| Volume (%) | 113 | 100 | 100 | 114 | 115 | 117 |
| Oven spring | 3 | 1 | 2 | 4 | 4 | 4 |
| Dough Stability | 3 | 2 | 2 | 5 | 4 | 4 |
| Crumb structure | 3 | 2 | 2 | 5 | 4 | 4 |

TABLE 5

Baking performance of the lipolytic enzyme LIP02 at different doses (mg protein per kg flour (determined according to Bradford))

| | Control (DATEM) | Blank (0) | 0.5 | 1 | 2.5 |
|---|---|---|---|---|---|
| Volume (%) | 113 | 100 | 100 | 111 | 115 |
| Oven spring | 3 | 1 | 2 | 4 | 4 |
| Loaf shape | 3 | 2 | 2 | 4 | 5 |
| Crumb structure | 3 | 2 | 2 | 5 | 5 |

Example 5

Baking Experiment—Full Scale Batard

The baking performance of the lipolytic enzymes LIP01-LIP02 was also tested in full scale batard. 3000 g of flour (Kolibri™), 70 g compressed yeast, 60 g salt, 50 ppm ascorbic acid, 2 ppm Bakezyme® P500 (fungal alpha-amylase), 15 ppm Bakezyme® HSP6000 (fungal hemicellulase) and 1740 ml water was mixed in a Diosna mixer for 2 minutes at speed 1 and 100 Wh in speed 2, to a final dough temperature of 27° C. The dough was divided in 6 pieces of 350 g, rounded and proofed for 20 minutes at 32° C. and 90% relative humidity. Afterwards the dough pieces were moulded and shaped and proofed for 100 minutes at 34° C. at relative humidity of 90%. The fully proofed dough pieces were incised and baked in an oven at 240° C. for 30 minutes with initial steam addition.

The various effects of the lipolytic enzyme at different doses, both on dough and the final baked product, were compared to a blank, a loaf containing no extra additions, and a control loaf containing 0.3% DATEM (Panodan® 80CP). After cooling down to room temperature the volumes of the loaves were determined by an automated bread volume analyser (BVM-3, RI Cards Instruments AB, Viken, Sweden). The other effects were evaluated manually and visually by an experienced baker according to the scales depicted in Table 6. The results are given in Tables 7 and 8.

TABLE 6

Scores for effects observed in full scale batard

| Effect | Score | | | | |
|---|---|---|---|---|---|
| | 1 | 2 | 3 | 4 | 5 |
| Dough stickiness | very sticky | sticky | Control bread | Much better | excellent dry |
| Dough extensibility | Very short | shorter than control | Control bread | Good | too extensible |
| Blistering | very weak, having many blisters | weak, having few blisters | Control bread | More stable than control | excellently stable |
| Oven spring | incision closed completely | incision closed partially | Control bread | Completely open incision | completely open incision; teared |
| Dough Stability | flat | medium | Control bread | height/width ratio better than (3) | height/width ratio better than (3), spherical cross-section |
| Crust colour | Very light | light | Control bread | Excellent | too dark |
| Crumb structure | poor | non-uniform | Control bread | Good | excellent |
| Crumb colour | Off-white and greyish | off-white | Control bread | More white than control | excellently white |

TABLE 7

Baking performance of the lipolytic enzyme LIP01 at different doses (mg protein per kg flour (determined according to Bradford)

|  | Control (DATEM) | Blank (0) | 0.75 | 1 | 1.7 | 2.4 | 3.8 |
|---|---|---|---|---|---|---|---|
| Volume (%) | 119 | 100 | 95 | 104 | 112 | 126 | 123 |
| Dough stickiness | 3 | 3 | 3 | 3 | 3 | 3 | 3 |
| Dough extensibility | 3 | 3 | 3 | 3 | 4 | 4 | 4 |
| Blistering | 3 | 2 | 2 | 3 | 4 | 5 | 4 |
| Oven spring | 3 | 1 | 2 | 3 | 4 | 5 | 5 |
| Dough stability | 3 | 2 | 3 | 4 | 4 | 4 | 4 |
| Crust colour | 3 | 3 | 3 | 3 | 3 | 3 | 3 |
| Crumb structure | 3 | 2 | 2 | 3 | 4 | 5 | 4 |
| Crumb colour | 3 | 2 | 2 | 3 | 3 | 4 | 4 |

TABLE 8

Baking performance of the lipolytic enzyme LIP02 at different doses (mg protein per kg flour (determined according to Bradford)

|  | Control (DATEM) | Blank (0) | 0.5 | 1 | 2 | 3 | 4 |
|---|---|---|---|---|---|---|---|
| Volume (%) | 119 | 100 | 96 | 104 | 117 | 119 | 118 |
| Dough stickiness | 3 | 3 | 3 | 3 | 3 | 3 | 3 |
| Dough extensibility | 3 | 3 | 3 | 3 | 4 | 4 | 4 |
| Dough stability | 3 | 2 | 2 | 3 | 4 | 5 | 4 |
| Oven spring | 3 | 1 | 2 | 3 | 4 | 5 | 5 |
| Loaf shape | 3 | 2 | 3 | 4 | 4 | 4 | 4 |
| Crust colour | 3 | 3 | 3 | 3 | 3 | 3 | 3 |
| Crumb structure | 3 | 2 | 2 | 3 | 4 | 5 | 4 |
| Crumb colour | 3 | 2 | 2 | 3 | 3 | 4 | 4 |

Example 6

Determination of Lipid Conversions in Dough of Mini-Batard

Polar Lipids

Lipids were extracted by vigorously shaking freeze-dried and grinded fully proofed dough (see Example 3) with water-saturated butanol. After centrifugation the clear supernatant is analysed on HPLC on LiChrospher 100 DIOL 5 μm (250×4.0 mm), lipoidic components were detected by Evaporative Light Scattering (Alltech ELSD 2000ES), at nitrogen flow of 1.5 l/min, temperature of 80° C., impactor on. Elution was performed using two mobile phases in a gradient program, at a flow of 1.0 ml/min:
A: heptane/isopropanol/butanol/tetrahydrofuran/iso-octan/water (64.5/17.5/7/5/5/1)
B: isopropanol/butanol/tetrahydrofuran/iso-octan/water (73/7/5/5/10).
To both elution solutions 77 μl ammoniac solution and 77 μl trifluor acetic acid is added per liter.
Gradient program: linear from 100% A to 100% B in 25 min, then 100% B for 5 min, then linear gradient from 100% B to 100% A for 0.5 min, and finally 100% A for 5 min with an injection volume of 20 μl and at a column temperature of 80° C. References of galactolipids, phospholipids, tri-, di- and monoglycerides, for example monogalactosyldiglyceride, monogalactosylmonoglyceride, digalactosyldiglyceride, digalactosylmonoglyceride, phosphatidylcholine and lyso-phosphatidylcholine, were used to indicate the elution order of the various compounds and calculate their response factors and amounts present in the dough.

In Tables 9 and 10 the amounts of the main polar lipids in fully proofed dough containing various amounts of LIP01-LIP02 are presented. It is clear from these results that LIP01-LIP02 efficiently converts galactosyldiglycerides to galactosylmonoglycerides at relatively low dose, with a preference for digalactosyldiglyceride in comparison to monogalactosyldiglyceride, and also in comparison to phosphatidylcholine.

It is furthermore clear that a dose of 2.4 ppm (Bradford protein) the optimal baking result of Example 4 coincides with the highest level of digalactosylmonoglyceride.

TABLE 9

Polar lipids in fully proofed dough (expressed as g per kg freeze-dried dough) containing various amounts of LIP01 (expressed as mg Bradford-protein per kg flour).

|  | MGDG | MGMG | DGDG | DGMG | PC | LPC |
|---|---|---|---|---|---|---|
| Blank (0 ppm) | 1.19 | 0.12 | 1.70 | 0.19 | 0.55 | 0.36 |
| LIP01 (0.6 ppm) | 0.78 | 0.26 | 0.48 | 1.13 | 0.47 | 0.35 |
| LIP01 (1.0 ppm) | 0.35 | 0.23 | 0.26 | 1.34 | 0.46 | 0.39 |
| LIP01 (2.4 ppm) | 0.35 | 0.15 | 0.17 | 1.63 | 0.42 | 0.28 |
| LIP01 (3.8 ppm) | 0.31 | 0.09 | 0.09 | 1.49 | 0.35 | 0.31 |

MGDG = monogalactosyldiglyceride; MGMG = monogalactosylmonoglyceride; DGDG = digalactosyldiglyceride; DGMG = digalactosylmonoglyceride; PC = phosphatidylcholine; LPC = lyso-phosphatidylcholine

TABLE 10

Polar lipids in fully proofed dough (expressed as g per kg freeze-dried dough) containing various amounts of LIP02 (expressed as mg Bradford-protein per kg flour).

|  | MGDG | MGMG | DGDG | DGMG | PC | LPC |
|---|---|---|---|---|---|---|
| Blank (0 ppm) | 1.69 | 0.41 | 2.30 | 0.32 | 0.47 | 1.30 |
| LIP02 (0.5 ppm) | 1.21 | 0.64 | 0.79 | 1.58 | 0.45 | 1.12 |
| LIP02 (1.0 ppm) | 1.10 | 0.69 | 0.37 | 1.80 | 0.41 | 1.11 |
| LIP02 (2.5 ppm) | 1.01 | 0.66 | 0.13 | 1.84 | 0.37 | 1.12 |

MGDG = monogalactosyldiglyceride; MGMG = monogalactosylmonoglyceride; DGDG = digalactosyldiglyceride; DGMG = digalactosylmonoglyceride; PC = phosphatidylcholine; LPC = lyso-phosphatidylcholine Apolar Lipids Apolar lipids are extracted by vigorously shaking freeze-dried and grinded fully proofed dough (see Baking Example 1) with heptane containing 1% acetic acid. After centrifugation the clear supernatant is analysed on HPLC on Spherisorb S3CN (Phenomenex OOD-0097-EO; 100×4.6 mm), lipoidic components are detected by Evaporative Light Scattering (Alltech ELSD 2000ES), at nitrogen flow of 1.5 l/min, temperature of 40° C., impactor off. Elution is performed using two mobile phases (A: heptane and B: tert-butyl-methyl ether containing 1% acetic acid) in the following linear gradient program, at a flow of 1.0 ml/min, injection volume 20 μl and ambient column temperature:

| Time (min) | A (%) | B (%) |
|---|---|---|
| 0 | 98 | 2 |
| 3 | 98 | 2 |
| 15 | 80 | 20 |
| 27 | 0 | 100 |
| 32 | 0 | 100 |
| 32.1 | 98 | 2 |
| 40 | 98 | 2 |

References of tri-, di-, monoglycerides and fatty acid are used to indicate the elution order of the various compounds and calculate their response factors and amounts present in the dough.

The invention claimed is:

1. An isolated polypeptide having lipolytic activity comprising an amino acid sequence that is at least 95% identical to the amino acid sequence according to SEQ ID NO: 8 or 9, with the proviso that the isolated polypeptide has an aspartic acid at a position corresponding to position 128 of SEQ ID NO: 8 or position 94 of SEQ ID NO: 9.

2. An isolated polypeptide according to claim 1, wherein said isolated polypeptide is a recombinant baking enzyme.

3. A method of preparing a dough comprising: adding the polypeptide according to claim 1 to at least one ingredient of the dough.

4. A dough comprising the polypeptide according to claim 1.

5. The dough according to claim 4 having improved dough stability.

6. The dough according to claim 4 having at least one of the improved properties selected from the group consisting of increased strength, increased elasticity, increased stability, reduced stickiness, and/or improved extensibility of the dough.

7. A method of preparing a baked product comprising: baking the dough according to claim 3.

8. A baked product obtainable by baking a dough according to claim 3.

9. The baked product according to claim 8 which is bread.

10. The baked product according to claim 8 having increased loaf volume.

11. The baked product according to claim 8 having at least one improved property selected from the group consisting of increased volume, improved flavor, improved crumb structure, improved crumb softness, reduced blistering and improved anti-staling.

12. The isolated polypeptide according to claim 1, obtained by expressing a polynucleotide that encodes said isolated polypeptide in an *Aspergillus niger* host cell.

13. The isolated polypeptide according to claim 1 consisting of SEQ ID NO: 8 or 9.

14. A pre-mix comprising flour and an isolated polypeptide according to claim 1.

15. A baking additive in the form of a granulate or agglomerated powder comprising an isolated polypeptide according to claim 1.

16. The baking additive according to claim 15, wherein more than 95% (by weight) of particles are in the range from 25 to 500 μm.

17. A composition comprising a polypeptide according to claim 1 and at least one additional enzyme useful for improving bread and/or dough.

18. The composition according to claim 17, wherein the additional enzyme is selected from the group consisting of amylase, cyclodextrin glucanotransferase, peptidase, transglutaminase, lipase, galactolipase, phospholipase, cellulase, hemicellulase, protease, protein disulfide isomerase, glycosyltransferase, peroxidase, laccase, and oxidase.

19. A method of production of digalactosylmonoglyceride from a digalactosyldiglyceride containing source comprising treatment of the digalactosyldiglyceride containing source with an enzyme comprising the isolated polypeptide according to claim 1.

20. A method of production of glucose syrups from wheat gluten comprising treatment of the wheat gluten with an enzyme comprising the isolated polypeptide according to claim 1 to remove the precipitate that occurs during saccharification of wheat gluten.

21. A method of degumming vegetable oils comprising treatment of the vegetable oils with an enzyme comprising the isolated polypeptide according to claim 1.

22. A method of modification of a phospholipid emulsifier comprising treatment of the emulsifier with an enzyme comprising the isolated polypeptide according to claim 1.

* * * * *